(12) United States Patent
Baim et al.

(10) Patent No.: US 8,747,456 B2
(45) Date of Patent: Jun. 10, 2014

(54) BIFURCATION STENT DELIVERY SYSTEM AND METHODS

(75) Inventors: Donald Baim, Westwood, MA (US);
David L. Friesen, Otsego, MN (US);
Richard Gunderson, Maple Grove, MN (US); Andrzej Malewicz, Minneapolis, MN (US); Michael Meyer, Richfield, MN (US); Daniel Quillin, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1490 days.

(21) Appl. No.: 12/347,919

(22) Filed: Dec. 31, 2008

(65) Prior Publication Data
US 2009/0171430 A1 Jul. 2, 2009

Related U.S. Application Data

(60) Provisional application No. 61/018,043, filed on Dec. 31, 2007.

(51) Int. Cl.
*A61F 2/06* (2013.01)

(52) U.S. Cl.
USPC ....... 623/1.35; 623/1.11; 623/1.23; 623/1.24; 623/1.27

(58) Field of Classification Search
USPC .................... 623/1.11, 1.35, 1.23, 1.24, 1.27
See application file for complete search history.

(56) References Cited

U.S. PATENT DOCUMENTS

| | | |
|---|---|---|
| 1,596,754 A | 8/1926 | Moschelle |
| 3,657,744 A | 4/1972 | Ersek |
| 3,872,893 A | 3/1975 | Roberts |
| 3,884,242 A | 5/1975 | Bazell et al. |

(Continued)

FOREIGN PATENT DOCUMENTS

| | | |
|---|---|---|
| CA | 2227446 | 12/1997 |
| CA | 220864 | 7/1999 |

(Continued)

OTHER PUBLICATIONS

Caputo et al., "Stent Jail: A Minimum-Security Prison," The American Journal of Cardiology, vol. 77, pp. 1226-1230, Jun. 1, 1996.

(Continued)

*Primary Examiner* — Victor Nguyen
*Assistant Examiner* — Kevin Everage
(74) *Attorney, Agent, or Firm* — Seager, Tufte & Wickhem LLC

(57) ABSTRACT

A catheter assembly may include a main balloon arranged to reside within the main vessel, and a branch balloon configured to extend from the main vessel into the branch vessel. A stent may be situated around the main balloon and may include a branch aperture at a location between proximal and distal open ends of the stent. The branch balloon may extend from within the stent, through the branch aperture, and into the branch vessel. The branch balloon, when inflated, may extend into the branch vessel. The main balloon, when inflated, may also expand the stent within the main vessel. In some arrangements, the branch balloon, when inflated, can function as an anchor within the branch vessel that resists radial and axial movement of the stent relative to the branch vessel and main vessel during expansion of the stent by the main balloon.

14 Claims, 10 Drawing Sheets

(56) References Cited

U.S. PATENT DOCUMENTS

| | | |
|---|---|---|
| 4,140,126 A | 2/1979 | Choudhury |
| 4,309,994 A | 1/1982 | Grunwald |
| 4,385,631 A | 5/1983 | Uthmann |
| 4,410,476 A | 10/1983 | Redding et al. |
| 4,413,989 A | 11/1983 | Schjeldahl et al. |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed |
| 4,762,128 A | 8/1988 | Rosenbluth |
| 4,769,005 A | 9/1988 | Ginsburg et al. |
| 4,769,029 A | 9/1988 | Patel |
| 4,774,949 A | 10/1988 | Fogarty |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,905,667 A | 3/1990 | Foerster et al. |
| 4,906,244 A | 3/1990 | Pinchuk et al. |
| 4,909,258 A | 3/1990 | Kuntz et al. |
| 4,946,464 A | 8/1990 | Pevsner |
| 4,950,227 A | 8/1990 | Savin et al. |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 4,998,923 A | 3/1991 | Samson et al. |
| 5,042,976 A | 8/1991 | Ishitsu et al. |
| 5,054,501 A | 10/1991 | Chuttani et al. |
| 5,059,170 A | 10/1991 | Cameron |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang et al. |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,244,619 A | 9/1993 | Burnham |
| 5,254,619 A | 10/1993 | Ando |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Cardon et al. |
| 5,387,235 A | 2/1995 | Chuter |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,476,471 A | 12/1995 | Shifrin et al. |
| 5,487,730 A | 1/1996 | Marcadis et al. |
| 5,489,271 A | 2/1996 | Andersen |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau et al. |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,201 A | 10/1996 | Burns |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,636,641 A | 6/1997 | Fariabi |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Marcade |
| 5,676,697 A | 10/1997 | McDonald |
| 5,679,400 A | 10/1997 | Tuch |
| 5,681,345 A | 10/1997 | Euteneuer |
| 5,683,450 A | 11/1997 | Goicoechea et al. |
| 5,683,451 A | 11/1997 | Lenker et al. |
| 5,690,642 A | 11/1997 | Osborne et al. |
| 5,693,084 A | 12/1997 | Chuter |
| 5,693,086 A | 12/1997 | Goicoechea et al. |
| 5,693,088 A | 12/1997 | Lazarus |
| 5,697,971 A | 12/1997 | Fischell et al. |
| 5,707,348 A | 1/1998 | Krogh |

(56) References Cited

U.S. PATENT DOCUMENTS

| | | |
|---|---|---|
| 5,707,354 A | 1/1998 | Salmon et al. |
| 5,709,713 A | 1/1998 | Evans |
| 5,716,365 A | 2/1998 | Goicoechea et al. |
| 5,718,683 A | 2/1998 | Ressemann et al. |
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,749,890 A | 5/1998 | Shaknovich |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,773 A | 5/1998 | Evans et al. |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,788,707 A | 8/1998 | Del Toro et al. |
| 5,792,105 A | 8/1998 | Lin et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,039 A | 10/1998 | Piplani et al. |
| 5,824,040 A | 10/1998 | Cox et al. |
| 5,824,041 A | 10/1998 | Lenker et al. |
| 5,824,042 A | 10/1998 | Lombardi et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,893,887 A | 4/1999 | Jayaraman |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane et al. |
| 5,938,696 A | 8/1999 | Goicoechea et al. |
| 5,948,016 A | 9/1999 | Jang |
| 5,951,599 A | 9/1999 | McCrory |
| 5,961,490 A | 10/1999 | Adams |
| 5,961,548 A | 10/1999 | Shmulewitz |
| 5,967,986 A | 10/1999 | Cimochowski et al. |
| 5,972,017 A | 10/1999 | Berg et al. |
| 5,972,018 A | 10/1999 | Israel et al. |
| 6,007,517 A | 12/1999 | Anderson |
| 6,013,054 A | 1/2000 | Jiun Yan |
| 6,013,091 A | 1/2000 | Ley et al. |
| 6,015,431 A | 1/2000 | Thornton et al. |
| 6,017,324 A | 1/2000 | Tu et al. |
| 6,017,363 A | 1/2000 | Hojelbane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | Von Oepen |
| 6,056,775 A | 5/2000 | Borghi et al. |
| 6,059,823 A | 5/2000 | Holman et al. |
| 6,059,824 A | 5/2000 | Taheri |
| 6,066,166 A | 5/2000 | Bischoff et al. |
| 6,066,168 A | 5/2000 | Lau et al. |
| 6,068,655 A | 5/2000 | Seguin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,096,045 A | 8/2000 | Del Toro et al. |
| 6,096,073 A | 8/2000 | Webster et al. |
| 6,099,497 A | 8/2000 | Adams et al. |
| 6,102,938 A | 8/2000 | Evans et al. |
| 6,113,579 A | 9/2000 | Eidenschink et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,143,002 A | 11/2000 | Vietmeier |
| 6,146,356 A | 11/2000 | Wang et al. |
| 6,152,945 A | 11/2000 | Bachinski et al. |
| 6,159,187 A | 12/2000 | Park et al. |
| 6,159,238 A | 12/2000 | Killion et al. |
| 6,165,195 A | 12/2000 | Wilson et al. |
| 6,165,197 A | 12/2000 | Yock |
| 6,165,214 A | 12/2000 | Lazarus |
| 6,168,621 B1 | 1/2001 | Vrba |
| 6,179,867 B1 | 1/2001 | Cox |
| 6,183,506 B1 | 2/2001 | Penn et al. |
| 6,183,509 B1 | 2/2001 | Dibie |
| 6,190,353 B1 | 2/2001 | Makower et al. |
| 6,190,403 B1 | 2/2001 | Fischell et al. |
| 6,193,746 B1 | 2/2001 | Strecker |
| 6,203,568 B1 | 3/2001 | Lombardi et al. |
| 6,203,569 B1 | 3/2001 | Wijay |
| 6,210,380 B1 | 4/2001 | Mauch |
| 6,210,429 B1 | 4/2001 | Vardi et al. |
| 6,210,431 B1 | 4/2001 | Power |
| 6,210,433 B1 | 4/2001 | Larre |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,097 B1 | 4/2001 | Wang et al. |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,251,133 B1 | 6/2001 | Richter et al. |
| 6,254,593 B1 | 7/2001 | Wilson |
| 6,258,073 B1 | 7/2001 | Mauch |
| 6,258,099 B1 | 7/2001 | Mareiro et al. |
| 6,258,115 B1 | 7/2001 | Dubrul |
| 6,258,116 B1 | 7/2001 | Hojeibane |
| 6,258,121 B1 | 7/2001 | Yang et al. |
| 6,258,534 B1 | 7/2001 | Laugharn, Jr. et al. |
| 6,261,273 B1 | 7/2001 | Ruiz |
| 6,261,305 B1 | 7/2001 | Marotta et al. |
| 6,261,316 B1 | 7/2001 | Shaolian et al. |
| 6,261,319 B1 | 7/2001 | Kveen et al. |

(56) References Cited

U.S. PATENT DOCUMENTS

| | | |
|---|---|---|
| 6,264,662 B1 | 7/2001 | Lauterjung |
| 6,264,682 B1 | 7/2001 | Wilson et al. |
| 6,264,686 B1 | 7/2001 | Rieu et al. |
| 6,273,911 B1 | 8/2001 | Cox et al. |
| 6,273,913 B1 | 8/2001 | Wright et al. |
| 6,287,277 B1 | 9/2001 | Yan |
| 6,287,314 B1 | 9/2001 | Lee et al. |
| 6,290,673 B1 | 9/2001 | Shanley |
| 6,293,967 B1 | 9/2001 | Shanley |
| 6,293,968 B1 | 9/2001 | Taheri |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,319,275 B1 | 11/2001 | Lashinski et al. |
| 6,325,821 B1 | 12/2001 | Gaschino et al. |
| 6,325,826 B1 | 12/2001 | Vardi et al. |
| 6,331,186 B1 | 12/2001 | Wang et al. |
| 6,334,864 B1 | 1/2002 | Amplatz et al. |
| 6,334,870 B1 | 1/2002 | Ehr et al. |
| 6,342,066 B1 | 1/2002 | Toro et al. |
| 6,346,089 B1 | 2/2002 | Dibie |
| 6,350,277 B1 | 2/2002 | Kocur |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,361,558 B1 | 3/2002 | Hieshima et al. |
| 6,371,978 B1 | 4/2002 | Wilson |
| 6,379,372 B1 | 4/2002 | Dehdashtian et al. |
| 6,383,213 B2 | 5/2002 | Wilson et al. |
| 6,383,215 B1 | 5/2002 | Sass |
| 6,387,120 B2 | 5/2002 | Wilson et al. |
| 6,395,018 B1 | 5/2002 | Castaneda |
| 6,398,792 B1 | 6/2002 | O'Connor |
| 6,398,804 B1 | 6/2002 | Spielberg |
| 6,428,567 B2 | 8/2002 | Wilson et al. |
| 6,428,570 B1 | 8/2002 | Globerman |
| 6,432,133 B1 | 8/2002 | Lau et al. |
| 6,436,090 B1 | 8/2002 | Sanchez et al. |
| 6,436,104 B2 | 8/2002 | Hojeibane |
| 6,436,134 B2 | 8/2002 | Richter et al. |
| 6,440,161 B1 | 8/2002 | Madrid et al. |
| 6,443,880 B2 | 9/2002 | Blais et al. |
| 6,468,302 B2 | 10/2002 | Cox et al. |
| 6,475,166 B1 | 11/2002 | Escano |
| 6,475,208 B2 | 11/2002 | Mauch |
| 6,478,814 B2 | 11/2002 | Wang et al. |
| 6,478,816 B1 | 11/2002 | Kveen et al. |
| 6,482,211 B1 | 11/2002 | Choi |
| 6,485,511 B2 | 11/2002 | Lau et al. |
| 6,488,694 B1 | 12/2002 | Lau et al. |
| 6,494,875 B1 | 12/2002 | Mauch |
| 6,494,905 B1 | 12/2002 | Zedler et al. |
| 6,508,836 B2 | 1/2003 | Wilson et al. |
| 6,511,504 B1 | 1/2003 | Lau et al. |
| 6,511,505 B2 | 1/2003 | Cox et al. |
| 6,514,281 B1 | 2/2003 | Blaesser et al. |
| 6,517,558 B2 | 2/2003 | Gittings et al. |
| 6,520,988 B1 | 2/2003 | Colombo et al. |
| 6,527,799 B2 | 3/2003 | Shanley |
| 6,540,719 B2 | 4/2003 | Bigus et al. |
| 6,540,779 B2 | 4/2003 | Richter et al. |
| 6,554,858 B2 | 4/2003 | Dereume et al. |
| 6,572,647 B1 | 6/2003 | Supper et al. |
| 6,576,009 B2 | 6/2003 | Ryan et al. |
| 6,579,309 B1 | 6/2003 | Loos et al. |
| 6,579,312 B2 | 6/2003 | Wilson et al. |
| 6,582,394 B1 | 6/2003 | Reiss et al. |
| 6,582,459 B1 | 6/2003 | Lau et al. |
| 6,596,020 B2 | 7/2003 | Vardi et al. |
| 6,596,022 B2 | 7/2003 | Lau et al. |
| 6,599,315 B2 | 7/2003 | Wilson |
| 6,599,316 B2 | 7/2003 | Vardi et al. |
| 6,602,284 B2 | 8/2003 | Cox et al. |
| 6,641,609 B2 | 11/2003 | Globerman |
| 6,645,241 B1 | 11/2003 | Strecker |
| 6,645,242 B1 | 11/2003 | Quinn |
| 6,652,573 B2 | 11/2003 | von Oepen |
| 6,669,717 B2 | 12/2003 | Marotta et al. |
| 6,676,667 B2 | 1/2004 | Mareiro et al. |
| 6,676,691 B1 | 1/2004 | Hosny |
| 6,679,911 B2 | 1/2004 | Burgermeister |
| 6,682,536 B2 | 1/2004 | Vardi et al. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,440 B2 | 3/2004 | Callol et al. |
| 6,736,841 B2 | 5/2004 | Musbach et al. |
| 6,746,411 B2 | 6/2004 | Khaw |
| 6,749,628 B1 | 6/2004 | Callol et al. |
| 6,770,092 B2 | 8/2004 | Richter |
| 6,776,793 B2 | 8/2004 | Brown et al. |
| 6,780,174 B2 | 8/2004 | Mauch |
| 6,802,856 B2 | 10/2004 | Wilson |
| 6,811,566 B1 | 11/2004 | Penn et al. |
| 6,827,735 B2 | 12/2004 | Greenberg |
| 6,827,736 B2 | 12/2004 | Perouse |
| 6,835,203 B1 | 12/2004 | Vardi et al. |
| 6,843,803 B2 | 1/2005 | Ryan et al. |
| 6,852,124 B2 | 2/2005 | Cox et al. |
| 6,855,125 B2 | 2/2005 | Shanley |
| 6,858,038 B2 | 2/2005 | Heuser |
| 6,884,258 B2 | 4/2005 | Vardi et al. |
| 6,890,349 B2 | 5/2005 | McGuckin, Jr. et al. |
| 6,896,699 B2 | 5/2005 | Wilson et al. |
| 6,905,477 B2 | 6/2005 | McDonnell et al. |
| 6,908,477 B2 | 6/2005 | McGuckin, Jr. et al. |
| 6,932,837 B2 | 8/2005 | Amplatz et al. |
| 6,939,368 B2 | 9/2005 | Simso |
| 6,942,689 B2 | 9/2005 | Majercak |
| 6,955,687 B2 | 10/2005 | Richter et al. |
| 6,955,688 B2 | 10/2005 | Wilson et al. |
| 6,962,602 B2 | 11/2005 | Vardi et al. |
| 6,980,174 B2 | 12/2005 | Flasza et al. |
| 7,004,963 B2 | 2/2006 | Wang et al. |
| 7,018,400 B2 | 3/2006 | Lashinski et al. |
| 7,056,323 B2 | 6/2006 | Mareiro et al. |
| 7,060,091 B2 | 6/2006 | Killion et al. |
| 7,105,019 B2 | 9/2006 | Hojeibane |
| 7,112,225 B2 | 9/2006 | Ginn |
| 7,118,593 B2 | 10/2006 | Davidson et al. |
| 7,125,419 B2 | 10/2006 | Sequin et al. |
| 7,163,553 B2 | 1/2007 | Limon |
| 7,220,275 B2 | 5/2007 | Davidson et al. |
| 7,225,518 B2 | 6/2007 | Eidenschink et al. |
| 7,238,197 B2 | 7/2007 | Sequin et al. |
| 7,244,853 B2 | 7/2007 | Schreiber et al. |
| 7,252,679 B2 | 8/2007 | Fischell et al. |
| 7,314,480 B2 | 1/2008 | Eidenschink et al. |
| 7,326,242 B2 | 2/2008 | Eidenschink |
| 7,334,557 B2 | 2/2008 | Callan |
| 7,341,598 B2 | 3/2008 | Davidson et al. |
| 7,344,514 B2 | 3/2008 | Shanley |
| 7,344,556 B2 | 3/2008 | Seguin et al. |
| 7,387,639 B2 | 6/2008 | Bourang et al. |
| 7,425,219 B2 | 9/2008 | Quadri |
| 7,476,243 B2 | 1/2009 | Eidenschink |
| 7,483,738 B2 | 1/2009 | Tamarkin et al. |
| 2001/0025195 A1 | 9/2001 | Shaolian et al. |
| 2001/0037146 A1 | 11/2001 | Lau et al. |
| 2001/0039448 A1 | 11/2001 | Dibie |
| 2002/0013618 A1 | 1/2002 | Marotta et al. |
| 2002/0032478 A1 | 3/2002 | Boekstegers et al. |
| 2002/0058990 A1 | 5/2002 | Jang |
| 2002/0123790 A1 | 9/2002 | White et al. |
| 2002/0156516 A1 | 10/2002 | Vardi et al. |
| 2002/0165604 A1 | 11/2002 | Shanley |
| 2002/0193872 A1 | 12/2002 | Trout, III et al. |
| 2002/0193873 A1 | 12/2002 | Brucker et al. |
| 2003/0009209 A1 | 1/2003 | Hojelbane |
| 2003/0009214 A1 | 1/2003 | Shanley |

(56) References Cited

U.S. PATENT DOCUMENTS

| | | | |
|---|---|---|---|
| 2003/0014102 A1 | 1/2003 | Hong et al. | |
| 2003/0055483 A1 | 3/2003 | Gumm | |
| 2003/0097169 A1 | 5/2003 | Brucker et al. | |
| 2003/0125802 A1 | 7/2003 | Callol et al. | |
| 2003/0144623 A1 | 7/2003 | Heath et al. | |
| 2003/0181923 A1 | 9/2003 | Vardi | |
| 2003/0195606 A1 | 10/2003 | Davidson et al. | |
| 2004/0015227 A1 | 1/2004 | Vardi et al. | |
| 2004/0044396 A1 | 3/2004 | Clerc et al. | |
| 2004/0049259 A1 | 3/2004 | Strecker | |
| 2004/0059406 A1 | 3/2004 | Cully et al. | |
| 2004/0117003 A1 | 6/2004 | Ouriel et al. | |
| 2004/0138737 A1* | 7/2004 | Davidson et al. | 623/1.35 |
| 2004/0148006 A1 | 7/2004 | Davidson et al. | |
| 2004/0167463 A1 | 8/2004 | Zawacki et al. | |
| 2004/0176837 A1 | 9/2004 | Atladottir et al. | |
| 2004/0186560 A1 | 9/2004 | Alt | |
| 2004/0225345 A1 | 11/2004 | Fischell et al. | |
| 2005/0004656 A1 | 1/2005 | Das | |
| 2005/0010278 A1 | 1/2005 | Vardi et al. | |
| 2005/0015108 A1 | 1/2005 | Williams et al. | |
| 2005/0060027 A1 | 3/2005 | Khenansho et al. | |
| 2005/0075722 A1 | 4/2005 | Chuter | |
| 2005/0096726 A1 | 5/2005 | Sequin et al. | |
| 2005/0102021 A1 | 5/2005 | Osborne | |
| 2005/0102023 A1 | 5/2005 | Yadin et al. | |
| 2005/0119731 A1 | 6/2005 | Brucker et al. | |
| 2005/0131526 A1 | 6/2005 | Wong | |
| 2005/0149161 A1 | 7/2005 | Eidenschink et al. | |
| 2005/0154442 A1 | 7/2005 | Eidenschink et al. | |
| 2005/0209673 A1 | 9/2005 | Shaked | |
| 2005/0228483 A1 | 10/2005 | Kaplan et al. | |
| 2005/0245941 A1 | 11/2005 | Vardi et al. | |
| 2006/0004323 A1* | 1/2006 | Chang et al. | 604/28 |
| 2006/0036315 A1 | 2/2006 | Yadin et al. | |
| 2006/0041303 A1 | 2/2006 | Israel | |
| 2006/0064064 A1 | 3/2006 | Jang | |
| 2006/0079956 A1 | 4/2006 | Eigler et al. | |
| 2006/0100694 A1 | 5/2006 | Globerman | |
| 2006/0173528 A1 | 8/2006 | Feld et al. | |
| 2007/0067019 A1* | 3/2007 | Miller et al. | 623/1.16 |
| 2007/0073376 A1 | 3/2007 | Krolik et al. | |
| 2007/0179591 A1 | 8/2007 | Baker et al. | |
| 2007/0203562 A1 | 8/2007 | Malewicz et al. | |
| 2008/0065141 A1 | 3/2008 | Holman et al. | |
| 2008/0086191 A1 | 4/2008 | Valencia et al. | |
| 2008/0255581 A1 | 10/2008 | Bourang et al. | |
| 2008/0288041 A1 | 11/2008 | Holman et al. | |
| 2009/0036830 A1* | 2/2009 | Jablonski et al. | 604/100.01 |

FOREIGN PATENT DOCUMENTS

| | | |
|---|---|---|
| CA | 2318314 | 7/1999 |
| CA | 2403826 | 9/2001 |
| CA | 2237829 | 11/2006 |
| DE | 9014845.2 | 9/1991 |
| DE | 29701883 | 3/1997 |
| DE | 29701758 | 5/1997 |
| DE | 60036233 | 5/2008 |
| EP | 0347023 | 12/1989 |
| EP | 0515201 | 3/1997 |
| EP | 0751752 | 6/1998 |
| EP | 0479557 | 7/1998 |
| EP | 0891751 | 1/1999 |
| EP | 0895759 | 2/1999 |
| EP | 0897700 | 2/1999 |
| EP | 0783873 | 4/2000 |
| EP | 1031328 | 8/2000 |
| EP | 0883384 | 12/2000 |
| EP | 0862 392 | 8/2001 |
| EP | 0808140 | 12/2001 |
| EP | 0698380 | 2/2002 |
| EP | 0884028 | 2/2002 |
| EP | 0705116 | 4/2002 |
| EP | 0646365 | 1/2004 |
| EP | 0684022 | 2/2004 |
| EP | 0897698 | 6/2004 |
| EP | 1182989 | 12/2004 |
| EP | 0937442 | 1/2005 |
| EP | 0551179 | 4/2005 |
| EP | 1157674 | 7/2005 |
| EP | 0804907 | 11/2005 |
| EP | 1031330 | 11/2005 |
| EP | 0170513 | 6/2006 |
| EP | 0876805 | 8/2006 |
| EP | 1190685 | 9/2006 |
| EP | 0880949 | 7/2007 |
| EP | 1512380 | 8/2007 |
| EP | 1031329 | 7/2008 |
| FR | 2337002 | 7/1977 |
| FR | 2678508 | 1/1993 |
| FR | 2740346 | 4/1997 |
| FR | 2756173 | 5/1998 |
| GB | 285530 | 2/1928 |
| GB | 2385530 | 8/2003 |
| JP | 8-299456 | 11/1996 |
| WO | WO 88/06026 | 8/1988 |
| WO | WO 90/13332 | 11/1990 |
| WO | WO 91/12779 | 9/1991 |
| WO | WO 92/14508 | 9/1992 |
| WO | WO 92/19308 | 11/1992 |
| WO | WO 93/04722 | 3/1993 |
| WO | WO 95/08965 | 4/1995 |
| WO | WO 95/21592 | 8/1995 |
| WO | WO 96/29955 | 10/1996 |
| WO | WO 96/34580 | 11/1996 |
| WO | WO 96/36269 | 11/1996 |
| WO | WO 96/41592 | 12/1996 |
| WO | WO 97/07752 | 3/1997 |
| WO | WO 97/09946 | 3/1997 |
| WO | WO 97/15346 | 5/1997 |
| WO | WO 97/16217 | 5/1997 |
| WO | WO 97/26936 | 7/1997 |
| WO | WO 97/32544 | 9/1997 |
| WO | WO 97/33532 | 9/1997 |
| WO | WO 97/41803 | 11/1997 |
| WO | WO 97/45073 | 12/1997 |
| WO | WO 97/46174 | 12/1997 |
| WO | WO 98/17204 | 4/1998 |
| WO | WO 98/19628 | 5/1998 |
| WO | WO 98/24104 | 6/1998 |
| WO | WO 98/35634 | 8/1998 |
| WO | WO 98/36709 | 8/1998 |
| WO | WO 98/37833 | 9/1998 |
| WO | WO 98/44871 | 10/1998 |
| WO | WO 98/47447 | 10/1998 |
| WO | WO 98/48733 | 11/1998 |
| WO | WO 98/48879 | 11/1998 |
| WO | WO 98/52497 | 11/1998 |
| WO | WO 99/00835 | 1/1999 |
| WO | WO 99/03426 | 1/1999 |
| WO | WO 99/04726 | 2/1999 |
| WO | WO 99/15103 | 4/1999 |
| WO | WO 99/17680 | 4/1999 |
| WO | WO 9915109 | 4/1999 |
| WO | WO 99/24104 | 5/1999 |
| WO | WO 99/34749 | 7/1999 |
| WO | WO 99/35979 | 7/1999 |
| WO | WO 99/36002 | 7/1999 |
| WO | WO 99/36015 | 7/1999 |
| WO | WO 99/39661 | 8/1999 |
| WO | WO 99/44539 | 9/1999 |
| WO | WO 99/49793 | 10/1999 |
| WO | WO 99/56661 | 11/1999 |
| WO | WO 99/58059 | 11/1999 |
| WO | WO 99/65419 | 12/1999 |
| WO | WO 00/00104 | 1/2000 |
| WO | WO 00/07523 | 2/2000 |
| WO | WO 00/10489 | 3/2000 |
| WO | WO 00/12166 | 3/2000 |
| WO | WO 00/13613 | 3/2000 |
| WO | WO 00/16719 | 3/2000 |
| WO | WO 00/27307 | 5/2000 |

(56) References Cited

FOREIGN PATENT DOCUMENTS

| | | |
|---|---|---|
| WO | WO 00/27463 | 5/2000 |
| WO | WO 0028922 | 5/2000 |
| WO | WO 00/44307 | 8/2000 |
| WO | WO 00/44309 | 8/2000 |
| WO | WO 00/48531 | 8/2000 |
| WO | WO 0047134 | 8/2000 |
| WO | WO 0049951 | 8/2000 |
| WO | WO 00/53122 | 9/2000 |
| WO | WO 0051523 | 9/2000 |
| WO | WO 00/57813 | 10/2000 |
| WO | WO 00/67673 | 11/2000 |
| WO | WO 00/71055 | 11/2000 |
| WO | WO 0071054 | 11/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/35715 | 5/2001 |
| WO | WO 01/35863 | 5/2001 |
| WO | WO 01/39697 | 6/2001 |
| WO | WO 01/39699 | 6/2001 |
| WO | WO 01/41677 | 6/2001 |
| WO | WO 01/43665 | 6/2001 |
| WO | WO 01/43809 | 6/2001 |
| WO | WO 01/45594 | 6/2001 |
| WO | WO 01/45785 | 6/2001 |
| WO | WO 01/49342 | 7/2001 |
| WO | WO 01/54621 | 8/2001 |
| WO | WO 01/54622 | 8/2001 |
| WO | WO 01/58385 | 8/2001 |
| WO | WO 01/60284 | 8/2001 |
| WO | WO 01/70294 | 9/2001 |
| WO | WO 01/70299 | 9/2001 |
| WO | WO 01/74273 | 10/2001 |
| WO | WO 01/89409 | 11/2001 |
| WO | WO 02/00138 | 1/2002 |
| WO | WO 02/053066 | 7/2002 |
| WO | WO 02/068012 | 9/2002 |
| WO | WO 02/076333 | 10/2002 |
| WO | WO 02/091951 | 11/2002 |
| WO | WO 02/094336 | 11/2002 |
| WO | WO 03/007842 | 1/2003 |
| WO | WO 03/055414 | 7/2003 |
| WO | WO 03/063924 | 8/2003 |
| WO | WO 2004/026174 | 4/2004 |
| WO | WO 2004/026180 | 4/2004 |
| WO | WO 2005/009295 | 2/2005 |
| WO | WO 2005/011528 | 2/2005 |
| WO | WO 2005/014077 | 2/2005 |
| WO | 2005041810 | 5/2005 |
| WO | WO 2005/107643 | 11/2005 |
| WO | WO 2006/028925 | 3/2006 |
| WO | WO 2006/033126 | 3/2006 |
| WO | 2006113838 | 10/2006 |
| WO | WO 2006/124162 | 11/2006 |
| WO | WO 2007/100672 | 9/2007 |

OTHER PUBLICATIONS

Carrie et al., "T-Shaped Stent Placement: A Technique for the Treatment of Dissected Bifurcation Lesions," Catheterization and Cardiovascular Diagnosis, vol. 37, pp. 311-313, 1996.

Chevalier et al., "Placement of Coronary Stents in Bifurcation Lesions by the "Culotte" Technique," The American Journal of Cardiology, vol. 82, pp. 943-949, Oct. 15, 1998.

Colombo et al., "Kissing Stents for Bifurcational Coronary Lesion," Catheterization and Cardiovascular Diagnosis, vol. 30, pp. 327-330, 1993.

U.S. Appl. No. 08/642,297, filed May 3, 1996, to Richter et al.
U.S. Appl. No. 09/325,996 filed Jun. 4, 1999, to Vardi et al.
U.S. Appl. No. 09/533,616, filed Mar. 22, 2000, to Vardi et al.
U.S. Appl. No. 09/614,472, filed Jul. 11, 2000, to Davidson et al.
U.S. Appl. No. 09/663,111, filed Sep. 15, 2000, to Davidson et al.
U.S. Appl. No. 12/183,163, filed Jul. 31, 2008, to Gunderson.
U.S. Appl. No. 12/183,869, filed Jul. 31, 2008, to Prindle et al.
U.S. Appl. No. 12/183,894, filed Jul. 31, 2008, to Tegels.

Dichek et al., "Seeding of Intravascular Stents with Genetically Engineered Endothelial Cells," Circulation, vol. 80, No. 5, pp. 1347-1353, Nov. 1989.

Fischman et al., "A Randomized Comparison of Coronary-Stent Placement and Balloon Angioplasty in the Treatment of Coronary Artery Disease," New England Journal of Medicine, vol. 331, No. 8, pp. 496-501, Aug. 25, 1994.

Katoh et al., "New Double Wire Technique to Stent Ostial Lesions," Catheterization and Cardiovascular Diagnosis, vol. 40, pp. 400-402, 1997.

Lear et al., "The Northridge Earthquake as a Trigger for Acute Myocardial Infarction," 1 page, 1996.

Lewis et al., "Acute Procedural Results in the Treatment of 30 Coronary Artery Bifurcation Lesions with a Double-Wire Atherectomy Technique for Side-Branch Protection," American Heart Journal, vol. 127, No. 6, pp. 1600-1607, 1994.

Nakamura et al., "Techniques for Palmaz-Schatz Stent Deployment in Lesions with a Large Side Branch," Catheterization and Cardiovascular Diagnosis, vol. 34, pp. 353-361, 1995.

Satler et al. "Bifurcation Disease: To Treat or Not to Treat," Catheterization and Cardiovascular Interventions, vol. 50, pp. 411-412, 2000.

SCIMED Life Systems, Inc., "TRIO 14 PTCA Catheter, Re-Engineering Over-The-Wire Balloon Technology," Brochure, 4 pages, 1994.

Serruys et al., "A Comparison of Balloon Expandable-Stent Implantation with Balloon Angioplasty in Patients with Coronary Artery Disease," The New England Journal of Medicine, vol. 331, No. 8, pp. 489-495, Aug. 25, 1994.

Yamashita et al., "Bifurcation Lesions: Two Stents Versus One Stent—Immediate and Follow-up Results," Journal of the American College of Cardiology, vol. 35, No. 5, pp. 1145-1151, Apr. 2000.

\* cited by examiner

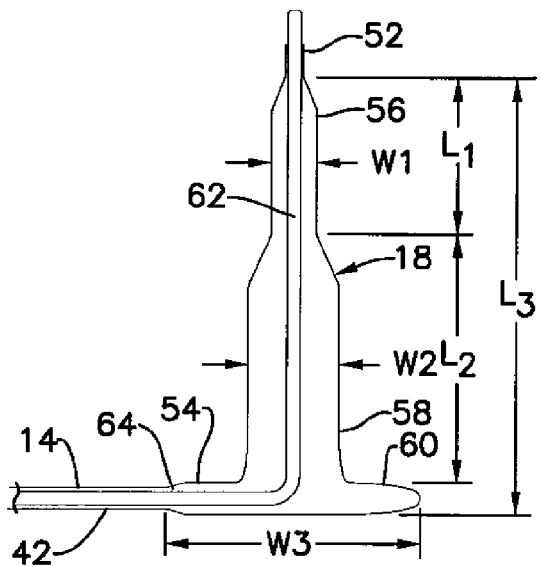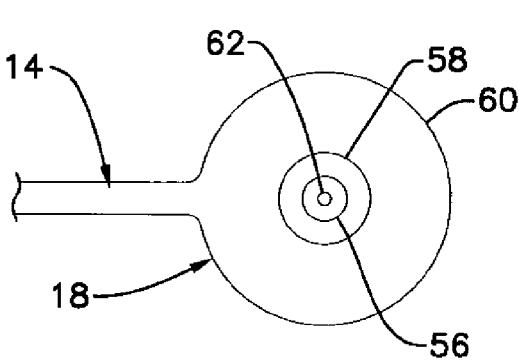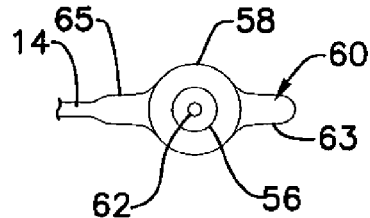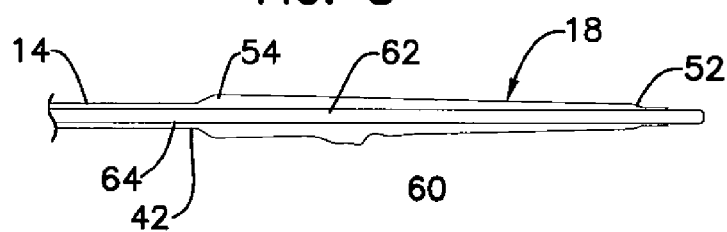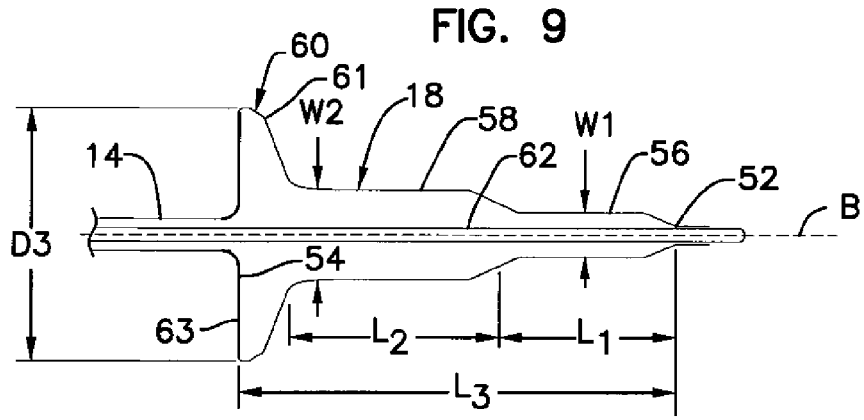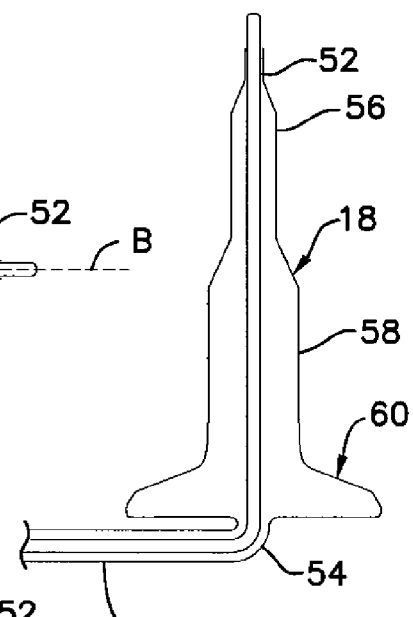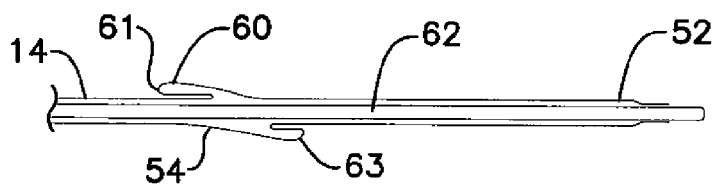

US 8,747,456 B2

BIFURCATION STENT DELIVERY SYSTEM AND METHODS

RELATED APPLICATIONS

This application claims priority to U.S. Provisional Application Ser. No. 61/018,043, filed Dec. 31, 2007, entitled "ALIGNMENT BALLOON FOR BIFURCATIONS STENT DELIVERY SYSTEM AND METHODS", the entirety of which is incorporated herein by reference.

FIELD

This disclosure relates generally to bifurcation treatment systems and methods of treating a bifurcated vessel. Example embodiments also relate to catheter configurations adapted for aligning and/or positioning features of the bifurcation treatment system relative to the bifurcated vessel.

BACKGROUND

Catheters can be used with stents and balloon inflatable structures to treat conditions such as strictures, stenoses, and narrowing in various parts of the body. Various catheter designs have been developed for the dilatation of stenoses and to deliver and deploy stents at treatment sites within the body.

Stents are typically intraluminally placed by a catheter within a vein, artery, or other tubular shaped body organ for treating conditions such as, for example, occlusions, stenoses, aneurysms, dissection, or weakened, diseased, or abnormally dilated vessel or vessel wall, by expanding the vessel or by reinforcing the vessel wall. Stents can improve angioplasty results by preventing elastic recoil and remodeling of the vessel wall and treating dissections in blood vessel walls caused by balloon angioplasty of coronary arteries.

While conventional stent technology is relatively well developed, stent technologies related to treatment of the region of a vessel bifurcation are still being developed. One challenge related to treatment of a vessel bifurcation involves alignment of the stent relative to the vessel branches of the vessel bifurcation. Another challenge relates to removal of the bifurcation treatment catheter from the vessel bifurcation treatment site.

SUMMARY OF THE DISCLOSURE

The illustrated examples disclosed herein relate generally to catheter assemblies and methods for treatment of a vessel bifurcation. An example catheter assembly may include a main balloon arranged to reside within the main vessel, and a branch balloon configured to extend from the main vessel into the branch vessel. In this arrangement, the main balloon may extend through the stent between open proximal and distal ends of the stent. The branch balloon may extend from within the stent, through a branch aperture in the stent, and into the branch vessel. The catheter assembly may be configured to inflate the branch balloon to extend the branch balloon into the branch vessel, and inflate the main balloon to expand the stent within the main vessel. The branch balloon may function as a guide that helps maintain radial and axial alignment of the stent branch aperture relative to an ostium of the branch vessel during expansion of the stent by the main balloon. The branch balloon may be positioned on the main balloon. Alternatively, the branch balloon may be positioned at an end portion of a branch catheter shaft that extends adjacent to a main catheter shaft, wherein the main catheter shaft has the main balloon positioned at a distal end portion thereof.

BRIEF DESCRIPTION OF THE DRAWINGS

FIG. 7 is a schematic side view of the branch catheter shown in FIGS. 1-6 in an inflated state;

FIG. 7A is a schematic top view of the branch catheter shown in FIG. 7 including an example base portion configuration for the branch balloon;

FIG. 7B is a schematic top view of the branch catheter shown in FIG. 7 including another example base portion configuration for the branch balloon;

FIG. 8 is a schematic side view of the branch catheter shown in FIG. 7 in another example deflated state arrangement;

FIG. 9 is a schematic side view of an example branch catheter with an inflated branch balloon arrangement in accordance with principles of the present disclosure;

FIG. 9A is a schematic side view of the branch catheter shown in FIG. 7 with the branch balloon directed at an angle relative to a main shaft of the branch catheter;

FIG. 10 is a schematic side view of the branch catheter shown in FIG. 7 with the branch balloon in a deflated state;

DETAILED DESCRIPTION

Figure 1:
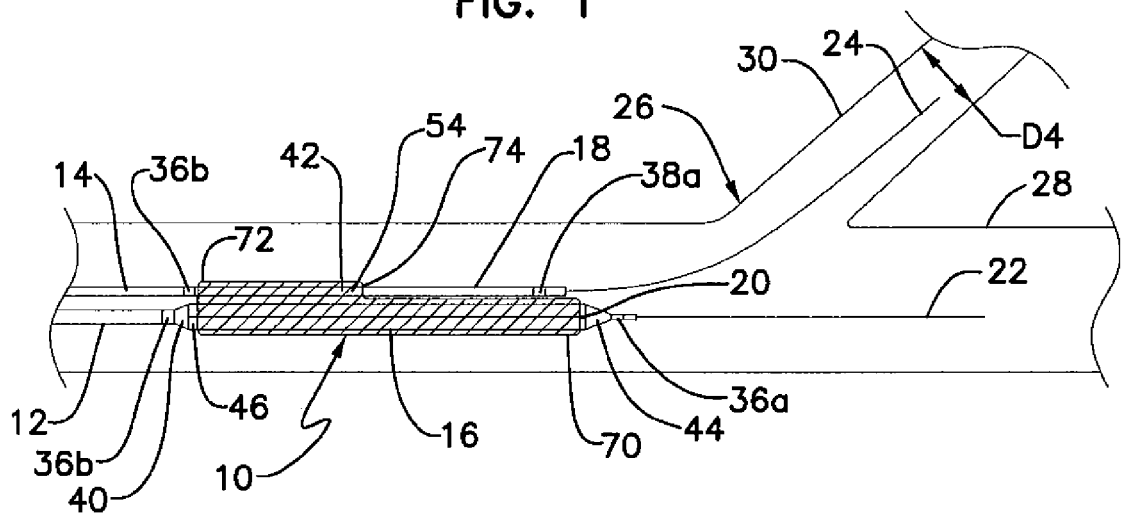
FIG. 1 is a schematic side view of an example catheter assembly in accordance with principles of the present disclosure, wherein the catheter assembly is positioned adjacent to a vessel bifurcation.

This disclosure relates to bifurcation treatment systems and related methods of treating bifurcations in a patient's body. Bifurcations typically include a main lumen and a branch lumen that extends or branches off from the main lumen. An example bifurcation is a vessel bifurcation. A vessel bifurcation can be defined with a parent or first vessel that splits into at least two branch vessels. Alternatively, a vessel bifurcation can be defined as a continuous main vessel with at least one branch vessel that branches off from the main vessel.

The disclosed systems and methods can include a main catheter branch, a side catheter branch, and an inflatable member (e.g., second balloon or side balloon) which when inflated extends in a direction generally radially away from the main catheter branch. The inflatable member can be positioned on the side catheter branch or on the main catheter branch. The term side catheter branch is defined as a portion of a catheter assembly that is configured to extend from a main vessel into a branch vessel of a vessel bifurcation. Typically, the side catheter branch defines a branch guidewire lumen sized for passing the side catheter branch over a guidewire and into the branch vessel. The term main catheter branch is defined as a portion of a catheter assembly that remains in a first vessel of a vessel bifurcation when the side catheter branch is positioned within a vessel branching from the first vessel. The inflatable member can be part of the main catheter branch or the side catheter branch.

In one example, the main catheter branch can include first and second balloon portions. The first balloon portion is an elongate balloon positioned at a distal end portion of the main catheter branch. The second balloon portion is positioned on the side catheter branch. In another example, the main catheter branch includes first and second balloon portions wherein the first balloon portion is an elongate balloon and the second balloon portion extends from a sidewall of the first balloon. The second balloon portion can be integral with the first balloon portion. The first and second balloon portions can be in fluid communication with each other. Alternatively, the first and second balloon portions can be fluidly separated and configured to inflate separate from each other.

The second balloon portion can include a variable width dimension at different locations along its length (e.g., a variable width at different locations between proximal and distal ends of the second balloon if the second balloon has as circular cross section). For example, one second balloon configuration includes a tapered balloon that decreases in width from the proximal end portion to the distal end portion of the second balloon. A maximum width dimension of that portion of the second balloon that is configured to extend into the branch vessel is sized smaller than the minimum internal width dimension of the branch vessel in that portion of the branch vessel into which the second balloon extends. That portion of the branch vessel into which the second balloon extends from the ostium of the branch vessel a distance along an longitudinal axis of the branch vessel a distance no greater than a total length of the branch balloon.

The second balloon portion can be configured and arranged to extend at an angle relative to a longitudinal dimension of the main balloon. The angle of extension can be between 0° and 90°, and more preferable between about 30° and 60°. The second balloon can be integral with the main balloon. The second balloon can also be positioned on a side inflation lumen that extends adjacent to the main balloon.

The main catheter shaft of the catheter assembly can be configured to define multiple guidewire lumens. The main catheter shaft can also be configured to define at least one inflation lumen in addition to at least one guidewire lumen. In other arrangements, the main and guidewire members defining the main and branch guidewire lumens are secured together or formed integral with each other at a location proximal of the main balloon.

An example catheter assembly 10 having inventive features in accordance with the present disclosure is shown and described with reference to FIGS. 1-13. Catheter assembly 10 includes a main catheter shaft 12, a branch catheter shaft 14, a main balloon 16, a branch balloon 18, a stent 20, and main and branch guidewires 22, 24. Catheter assembly 10 is shown in FIGS. 1-5 with reference to a vessel bifurcation 26 having a main vessel 28 and a branch vessel 30.

The main catheter shaft 12 has a distal end portion 40 adapted for positioning within a patient, and a proximal end portion (not shown) adapted for positioning outside of the patient. The branch catheter shaft 14 extends side-by-side with the main catheter shaft 12. The branch catheter shaft 14 includes a distal end 42. A proximal end portion (not shown) of the branch catheter shaft 14 can be integrated into the main catheter shaft 12 at a location distal of a proximal end portion of the main catheter shaft 12 and proximal of the stent 20. Alternatively, the branch catheter shaft 14 can extend separate from the main catheter shaft 12 from the distal end portion 42 to a location outside of the patient.

The main balloon 16 is positioned at the distal end portion 40 of the main catheter shaft 12. The main balloon 16 is an elongate tube-shaped structure sized to traverse the vessel bifurcation 26 (i.e., extend within the main vessel 28 from a proximal side to a distal side of an ostium of branch vessel 30). The main balloon branch 16 includes distal and proximal ends 44, 46, a main guidewire housing 47 defining a main guidewire lumen 48, and an inflation lumen 50 that extends in fluid communication with an interior of the main catheter shaft 12. The main balloon 16 is inflatable from the deflated state shown in FIG. 1 to the inflated state shown in FIG. 4 upon filling of the main balloon 16 with inflation fluid. The main balloon 16 is deflatable upon removal of the inflation fluid through the inflation lumen 50 and proximally out through the main catheter shaft 12.

The branch balloon 18 is positioned at the distal end portion 42 of the branch catheter shaft 14. The branch lumen 18 includes distal and proximal ends 52, 54, a first portion 56 having a maximum width dimension W1, a second portion 58 having a maximum width dimension W2, and a base portion 60 having a maximum width dimension W3 (see FIG. 7). The branch balloon 18 further includes a branch guidewire housing 61 defining a branch guidewire lumen 62 that extends between the proximal and distal ends 52, 54 and an inflation lumen 64 that is in fluid communication with an interior of the branch catheter shaft 14 (see FIG. 7). The branch balloon 18 can have a generally cylindrical or conical tube-shaped structure with a radially concentric cross-sectional shape at each point along its length between ends 52, 54.

Upon inflation, the branch balloon 18 extends at an acute branch angle β (see FIG. 3) measured between a longitudinal axis A of the main balloon 16 and a longitudinal axis B of the branch balloon 18. The angle β typically is in the range of 20 to 90° inclusive, and more typically about 45° to about 75° inclusive. The angle β is typically measure within a plane that is aligned along the axis A. The angle β is also typically arranged facing in a direction toward the distal portion of the main balloon 16. The angle β is typically measured when in a rest state with the main and branch balloons inflated. A rest state is a state for the catheter assembly when no external forces are applied move the main and branch balloons relative to each other. The catheter assembly configurations disclosed herein can be used with vessel bifurcations having an angled relationship between the branch and main vessel that is outside of the range of 20° to 90° for the angle β.

Materials used in the balloons, catheter shafts, and other components of the catheter assemblies disclosed herein can be made of any suitable material including, for example, thermoplastic polymers, polyethylene (high density, low density, intermediate density, linear low density), various co-polymers and blends of polyethylene, ionomers, polyesters, polycarbonates, polyamides, poly-vinyl chloride, acrylonitrile-butadiene-styrene copolymers, polyether-polyester copolymers, and polyetherpolyamide copolymers. One suitable material is Surlyn®, a copolymer polyolefin material (DuPont de Nemours, Wilmington, Del.). Still further suitable materials include thermoplastic polymers and thermoset polymeric materials, poly(ethylene terephthalate) (commonly referred to as PET), thermoplastic polyamide, polyphenylene sulfides, polypropylene. Some other example materials include polyurethanes and block copolymers, such as polyamide-polyether block copolymers or amide-tetramethylene glycol copolymers. Additional examples include the PEBAX® (a polyamide/polyether/polyester block copolymer) family of polymers, e.g., PEBAX® 70D, 72D, 2533, 5533, 6333, 7033, or 7233 (available from Arkema, Philadelphia, Pa.).

Other examples include nylons, such as aliphatic nylons, for example, Vestamid L2101 1F, Nylon 11 (Arkema), Nylon 6 (Honeywell), Nylon 6/10 (BASF), Nylon 6/12 (Ashley Polymers), or Nylon 12. Additional examples of nylons include aromatic nylons, such as Grivory (EMS) and Nylon MXD-6. Other nylons and/or combinations of nylons can also be used. Still further examples include polybutylene terephthalate (PBT), such as CELANEX® (available from Ticona, Summit, N.J.), polyester/ether block copolymers such as ARNITEL® (available from DSM, Erionspilla, Ind.), e.g., ARNITEL® EM740, aromatic amides such as Trogamid (PA6-3-T, Degussa), and thermoplastic elastomers such as HYTREL® (Dupont de Nemours, Wilmington, Del.). In some embodiments, the PEBAX®, HYTREL®, and ARNITEL® materials have a Shore D hardness of about 45D to about 82D. The balloon materials can be used pure or as blends. For example, a blend may include a PBT and one or more PBT thermoplastic elastomers, such as RITEFLEX® (available from Ticona), ARNITEL®, or HYTREL®, or polyethylene terephthalate (PET) and a thermoplastic elastomer, such as a PBT thermoplastic elastomer. Additional examples of balloon material can be found in U.S. Pat. No. 6,146,356. It should be understood that the specific materials disclosed below for the individual embodiments does not limit the embodiment to those materials.

The forming of balloons 16, 18 using the above listed materials can be determined, within a range, by controlling blowing conditions such as initial dimensions of tubing, pre-stretching, hoop ratio, heat set conditions, grinding and laser ablation of the tube. Compliance characteristics for balloon 16, 18 made from these example materials ranging from non-compliant to compliant characteristics. In one example, the balloon has wall strengths in excess of 20,000 psi.

Figure 3:
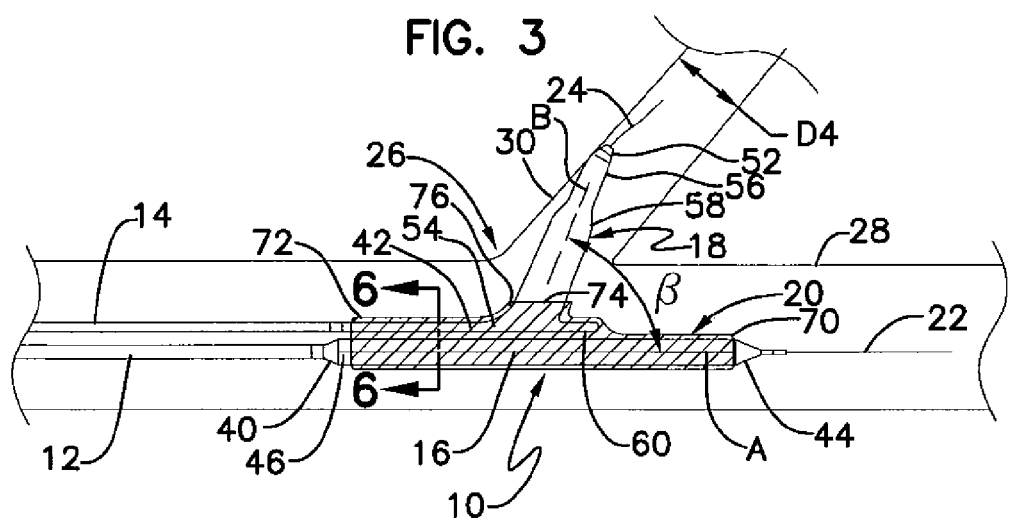
FIG. 3 is a schematic side view of the catheter assembly shown in FIG. 1 with a branch balloon of the catheter assembly inflated within the branch vessel of the vessel bifurcation.

FIGS. 3 and 7 illustrate the variable width structure of the branch balloon 18. The first portion 56 is positioned near the distal end portion 52. The first portion 56 has a maximum width $W_1$ that is less than the maximum width $W_2$ of the second portion 58. The widths $W_1$, $W_2$ are smaller than a width $W_4$ of the branch vessel 30, wherein the width $W_4$ is determined with or without the inclusive of any plaque present along the branch vessel 30. The maximum width dimension $W_3$ of the base portion 60 is greater than a maximum width dimension $W_4$ of a branch aperture 74 of the stent 20 (see FIG. 4) with the branch balloon 18 inflated. The base portion 60 is retained within the stent 20 due in part to the grater size of width $W_3$ relative to the maximum size $W_4$ of the branch aperture 74. The width $W_1$ can improve insertability of the branch balloon 18 into the branch vessel 30. The size of width $W_2$, which is greater than $W_1$ and smaller than $W_3$ is sized to minimize the amount of space between the interior of branch vessel 30 and the branch balloon 18 to help reduce the amount of axial and radial movement of the catheter assembly 10 relative to the branch vessel 30.

The first portion 56 has a length $L_1$, the second portion 58 has a length $L_2$, and the overall length of the branch balloon 18 between the base portion 60 and the distal end portion 52 has a length $L_3$ (see FIG. 7). The lengths $L_1$-$L_3$ can vary in different applications to vary the performance characteristics of the branch balloon 18. In one example, the length $L_3$ is greater than the width $W_4$ of the branch vessel 30. In another example, the length $L_3$ is at least as great as the width $W_2$ of the second portion 56. In some configurations, the length L3 is about 100% to 500% of the maximum value of width $W_2$. In other configurations, the length $L_3$ is about 100% to 200% of the width $W_5$ at the ostium of branch vessel 30 (see FIG. 5). The branch balloon 18, when inflated and before inflation of the main balloon 16, preferably extends into the branch vessel 30 a distance at least as great as the width $W_5$ at the ostium of branch vessel 30.

Typically, a longer balloon can help maintain the axial and radial orientation of the catheter assembly relative to an ostium of a branch vessel better than a shorter balloon having the same widths. Typically, a balloon that is too short can risk losing the desired axial and radial orientation after the desired orientation has been obtained. Changing the widths $W_1$-$W_3$ can also influence the performance characteristics of the branch balloon 18. Achieving optimum length features, ratios of lengths to the various widths, and the widths alone of the branch balloon 18 can influence how well the branch balloon 18 operates in a given vessel bifurcation environment. The width of features of the branch balloon 18, particularly at the base 60 and second portion 58 can influence how much resistance to radial and longitudinal movement of the catheter system 10 is applied during inflation of the main balloon 16.

Providing a branch balloon that is positioned along a branch vessel guidewire lumen and tapered towards the distal end portion helps to maintain an elongate, low profile branch balloon when the branch balloon is deflated. An elongate, low profile branch balloon can improve the retractability of the branch balloon from a stent that is deployed at a vessel bifurcation by reducing potential catch points where the balloon might catch on the stent while being removed.

In addition to varying the size (e.g., circumference, diameter or length) of the branch balloon 18, the shape and materials of the branch balloon can vary for different portions of the branch balloon 18. For example, the cross-sectional shape of the first and second portions 56, 58 can be oval, triangular, or polygonal rather than circular. Also, the materials used in the first portion 56 can be different than the materials used for the second portion 58 and the base 60. Varying the size, shape and materials of the branch balloon 18 can result in optimization of the performance characteristics of each portion of the branch balloon 18 for its intended purpose.

FIGS. 7A and 7B illustrate different structures for the base portion 60. FIG. 7A illustrates the base portion 60 as a disk shaped member having a generally constant diameter. FIG. 7B illustrates the base portion 60 having members 65, 63 extending in the proximal and distal directions. FIG. 7B does not include portions of the base 60 extending in the transverse direction (e.g., the direction perpendicular to the longitudinal axis of the catheter assembly 10 in the deflated state).

The branch balloon 18 shown in FIGS. 1-8 is connected to the branch catheter shaft 14 at a peripheral edge of the base 60. FIGS. 9-13 illustrate other example branch balloons wherein the branch catheter shaft 14 is connected to the branch balloon 18 at a proximal end portion 54 of the balloon 18. In some arrangements, the balloon 18 is formed from the branch catheter shaft 14, whereas in other arrangements the balloon 18 is separately formed and then attached to the branch catheter shaft. The branch catheter shaft 14 is aligned along a central axis B extending through the first, second and base portions 56, 58, 60.

The branch balloon 18 of FIGS. 9-10 has a base portion 60 extending on opposing sides of the second portion 58 as first and second base portions 65, 63. FIG. 9 illustrates the branch balloon portion 18 extending from a distal end portion of the branch catheter shaft 14 in an inflated state in which the branch balloon 18 is unconstrained (e.g., before being positioned and inflated within stent 20). FIG. 9A illustrates an arrangement of the branch balloon 18 that typically results when the branch catheter shaft 14 and base portion 60 are positioned within a stent and the first and second portions 56, 58 extend through a branch aperture of the stent (e.g., through branch aperture 74 of stent 20 shown in FIG. 1. FIG. 10 illustrates the branch balloon 18 in a deflated state. The first and second base portions 65, 63 extend in the proximal and distal directions, respectively, when the balloon 18 is inflated (see FIG. 9A). When the first and second members 65, 63 are oriented facing distally and proximally as shown in FIG. 10, the base 60 can more easily inflate within the stent. In other embodiments (e.g., the arrangement of base 60 shown in FIG. 8) the members 65, 63 are not directed in either the proximal or distal direction when the branch balloon 18 is in a deflated state. Rather, as shown in FIG. 8, the base portion 60 is recessed to fit generally within an outer profile cylindrical circumference of the entire branch balloon 18 between the proximal and distal ends 54, 52.

Figure 11:
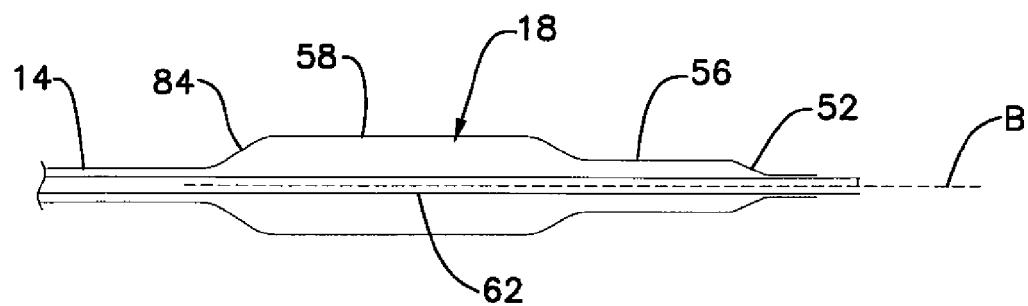
FIG. 11 is a schematic side view of a further example branch catheter with an inflated branch balloon arrangement in accordance with principles of the present disclosure.

FIG. 11 illustrates another example branch balloon 18 that does not include a defined base portion 60. The branch balloon 18 of FIG. 11 can be anchored or otherwise held relative to the stent 20 with an interference fit between the second portion 58 and the expandable structure 76 of stent 20 that surrounds the branch aperture 74.

Figure 12:
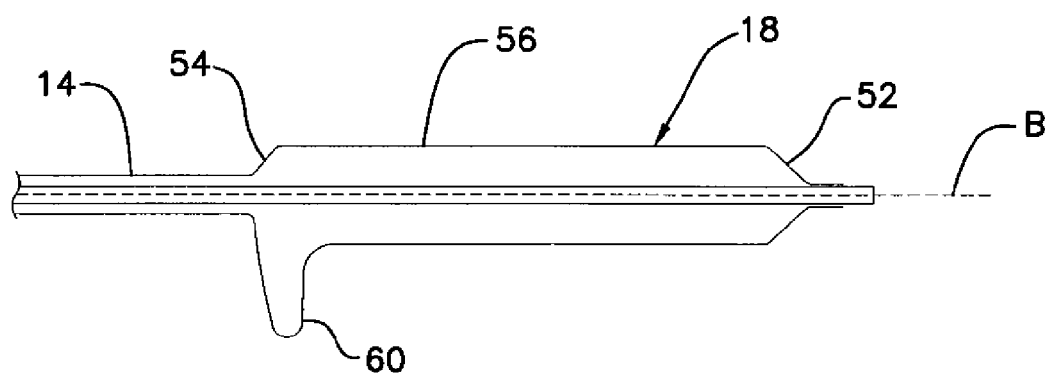
FIG. 12 is a schematic side view of a yet further example branch catheter with an inflated branch balloon arrangement in accordance with principles of the present disclosure.

FIG. 12 illustrates another example branch balloon 18 having a base portion 60 that extends transverse to only one side of the second portion 58. The use of any type of base portion 60 having a circumference or width measurement greater than a size of the branch aperture 74 of the stent 20 can help anchor or otherwise maintain a fixed relative position between the proximal end portion 54 of branch balloon 18 and the stent 20 at the proximal end portion 54 of the branch balloon 18. The base portion 60 can be referred to as a pylon or anchor structure for the branch balloon 18.

Figure 13:
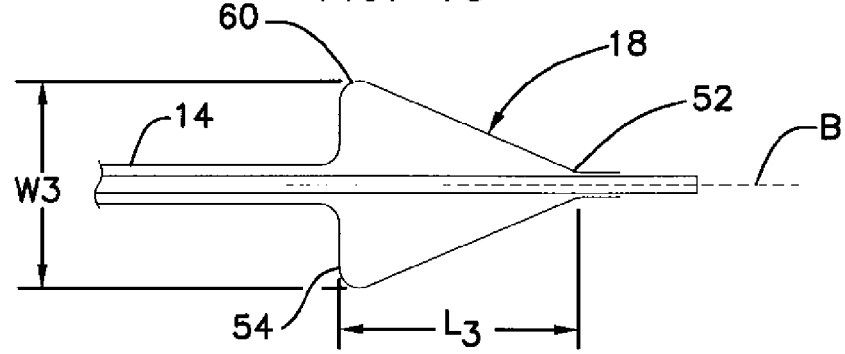
FIG. 13 is a schematic side view of a yet further example branch catheter with a conical shaped inflated branch balloon arrangement in accordance with principles of the present disclosure.
Figure 14:
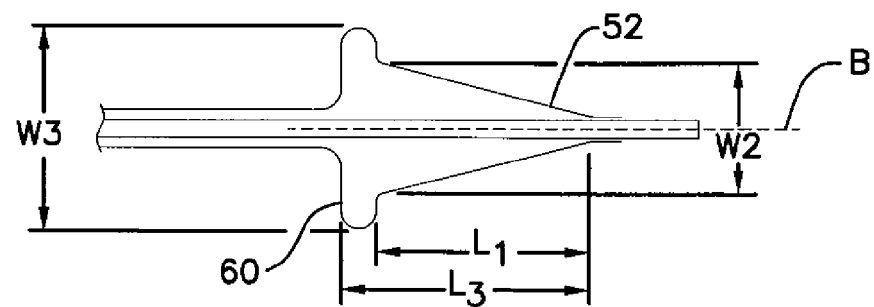
FIG. 14 is a schematic side view of a yet further example branch catheter with a conical shaped inflated branch balloon arrangement in accordance with principles of the present disclosure.

FIGS. 13 and 14 illustrate various conical shaped branch balloons 18. The balloon 18 shown in FIG. 13 has a base portion 60 at proximal end portion 54 having a maximum width dimension $W_3$ that tapers towards the distal end portion 52. The balloon 18 in FIG. 13 has a length $L_3$ from the proximal end portion 54 to the distal end portion 52. The balloon 18 shown in FIG. 14 has a base portion 60 having a maximum width dimension $W_3$, and a conical section that tapers from a maximum width dimension $W_2$ adjacent to the base portion 60 to the distal end portion 52. The balloon 18 shown in FIG. 14 has a total length $L_3$ from the proximal end portion 54 to the distal end portion 52, and a conical section length $L_3$ from the distal side of base 60 to the distal end portion 52. The lengths and widths of the balloons 18 shown in FIGS. 13 and 14 can vary in accordance within, for example, the ranges described above for the balloon 18 shown in FIGS. 9-10.

Referring now to FIGS. 1-5, an example method of treating the vessel bifurcation 26 with the catheter assembly 10 is described. First referring to FIG. 1, a distal end portion of the main guidewire 22 is inserted into the main vessel 28 beyond the ostium leading into branch vessel 30. A distal end portion of branch guidewire 24 is inserted through the ostium leading into the branch vessel 30 and into the branch vessel 30. The proximal end portions of guidewires 22, 24 (not shown) are inserted into the distal ends 44, 52 of the main and branch balloons 16, 18, respectively. The catheter assembly 10 is advanced over the guidewires 22, 24 into an area of the vessel bifurcation 26.

In alternative methods, only one of the guidewires 22, 24 is positioned within respective main and branch vessels 28, 30 prior to advancing the catheter assembly 10 to the area of the vessel bifurcation 26. In this alternative arrangement, the other of the guidewires 22, 24 is arranged as a fixed wire within the catheter assembly 10 and advanced with the catheter assembly 10 to the vessel bifurcation. Once the catheter assembly 10 has reached the vessel bifurcation, the guidewire fixed in the catheter assembly 10 is advanced into the targeted vessel that does not already have a guidewire positioned therein, and the catheter assembly is further advanced distally until radial and axial alignment of the stent branch aperture 74 with the ostium of branch vessel 30 is achieved.

Figure 2:
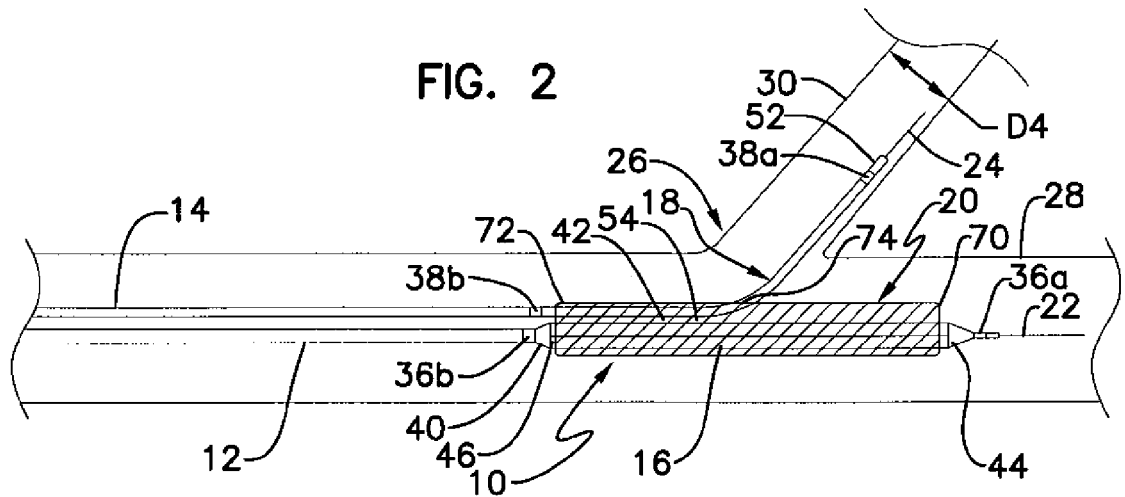
FIG. 2 is a schematic side view of the catheter assembly shown in FIG. 1 with a branch catheter of the catheter assembly positioned within a branch vessel of the vessel bifurcation.

Referring now to FIG. 2, the catheter assembly 10 is further advanced distally until the branch balloon 18 extends into the branch vessel 30. Minor adjustments to the radial and axial position of the catheter assembly 10 can be made in order to ensure that the branch aperture 74 of the stent 20 is positioned facing radially towards the opening or ostium into branch vessel 30. A plurality of markers 36a, b and 38a, b associated with the main and branch balloons 16, 18 can be used to help confirm the axial and radial alignment of the stent branch aperture 74 relative to the ostium of branch vessel 30. Various markers, marker materials, and marker arrangements for use as alignment features of catheter assembly 10 are described in U.S. Pat. No. 6,692,483 to Vardi, and co-pending U.S. Provisional Patent Application Ser. No. 60/776,149, filed on Sep. 22, 2006, and entitled Marker Arrangement for Bifurcation Catheter, which patent matters are incorporated herein by reference.

The branch balloon 18 in the inflated state shown in FIG. 3 can be used for visualization by the physician of portions of the catheter assembly even without the markers 36a, b. The inflation fluid used to fill the branch balloon 18 can include a contract agent that is visible under fluoroscopy. Further, the main and branch vessels 28, 30 into which the catheter assembly 10 is inserted can periodically be filled with a contrast agent that is also visible under fluoroscopy. Providing visualization of the vessels 28, 30 and the branch balloon 18 permits the physician to make radial and axial adjustments to the position of catheter assembly 10 to better ensure alignment of the stent branch aperture 74 relative to the ostium of branch vessel 30 before inflating main balloon 16.

Referring now to FIG. 3, the branch balloon 18 is inflated with inflation fluid that travels through branch catheter shaft 14 and into the branch balloon 18. The base portion 60 of the branch balloon 18 is retained within the stent 20. The first and second portions 56, 58 of the branch balloon 18 extend through the branch aperture 74 and into the branch vessel 30. As discussed above, the widths $W_1$, $W_2$ of the first and second portions 56, 58 are smaller than the widths W5 of the ostium of branch vessel 30. Preferably, there is little resistance to expansion of the branch balloon 18 except for the material of the branch balloon itself. Some resistance to expansion may be exerted by portions of the expandable stent structure 76 surrounding branch aperture 74. The first and second portions 56, 58 extend at an angle β from the main balloon 16.

Figure 4:
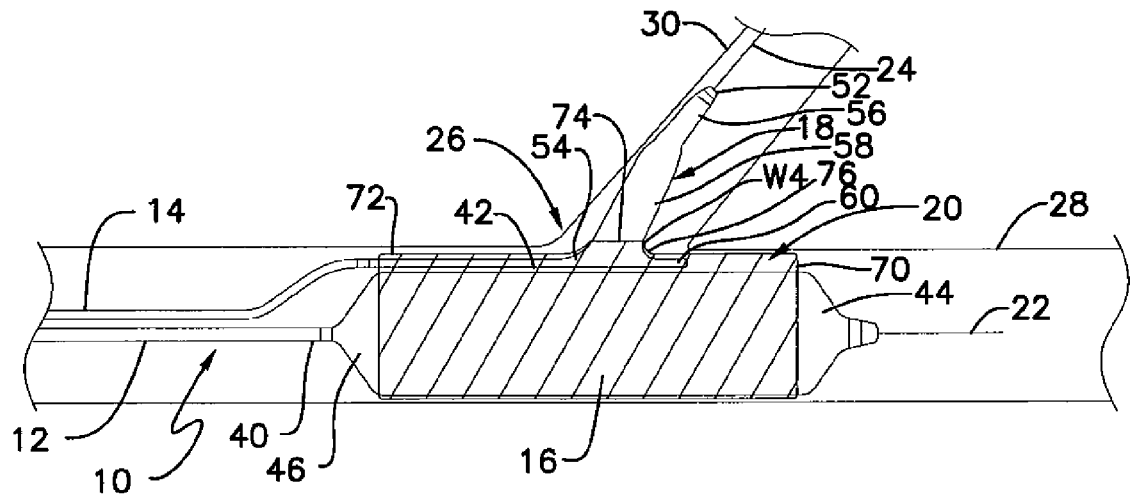
FIG. 4 is a schematic side view of the catheter assembly shown in FIG. 1 with the main and branch balloons inflated within the vessel bifurcation.

Referring now to FIG. 4, the main balloon 16 is inflated after the branch balloon 18 has been inflated. The main balloon 16 is inflated with inflation fluid that travels through main catheter shafts 14 and the inflation lumen 50. Typically, the stent 20 is secured to at least the main balloon 16 using an attachment method such as crimping, which permits release of the stent 20 from the balloon 16 after inflation of the balloon 16. The stent 20 may also be secured to the branch balloon 18 using a similar attachment method such as crimping. Due to the connection between stent 20 and main balloon 16, the stent 20 and main balloon 16 move axially and radially together relative to the vessel bifurcation 26. Since the branch balloon 18 extends in engagement with the stent 20 through the branch aperture 74 and into the branch vessel 30, the branch balloon 18 provides an axial and radial anchoring of the stent 20 and main balloon 16 as the main balloon 16 is inflated. Thus, the branch balloon 18, when inflated and positioned within the branch vessel 30 helps to maintain alignment of the branch aperture 74 with the ostium into branch vessel 30 during expansion of the stent 20 within main vessel 28.

After the stent 20 has been expanded as shown in FIG. 4, the main and branch balloons 16, 18 are deflated by removal of inflation fluid through the main and branch catheter shafts 12, 14. After deflation of balloons 16, 18, the catheter assembly 10 is removed proximally. The main guidewire 22 can also be removed at this time.

Figure 5:
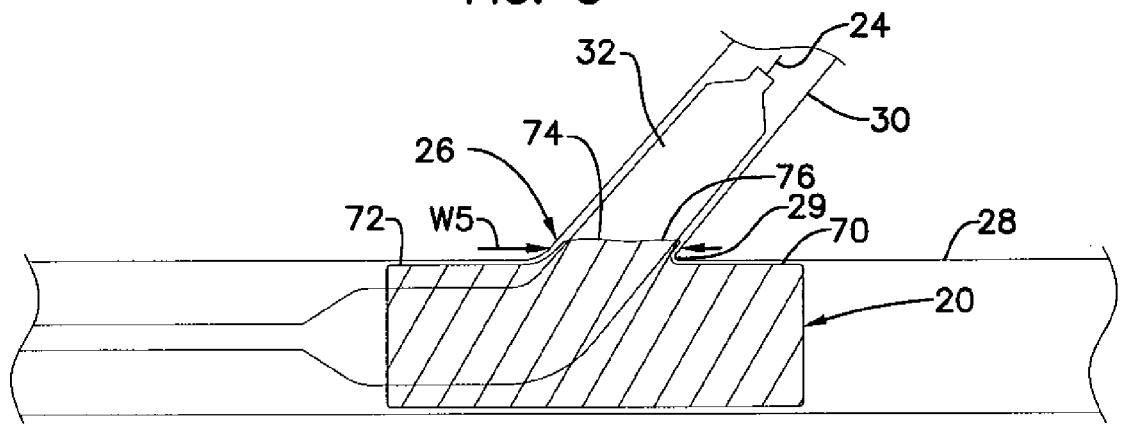
FIG. 5 is a schematic side view of the stent of the catheter assembly shown in FIG. 1 further expanded with a post delivery dilation catheter.
Figure 6:
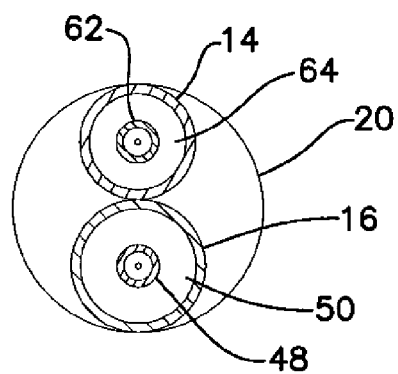
FIG. 6 is a schematic cross-sectional view of the catheter assembly shown in FIG. 3.

Referring now to FIG. 5, a separate dilation catheter 32 is advanced over the branch guidewire 24 through the interior of stent 20 and out of the branch aperture 74 into the branch vessel 30. The dilation catheter 32 is inflated to expand expandable structure surrounding the branch aperture 74 into the branch vessel 30. Preferably, the dilation catheter 32 expands the expandable structure surrounding the branch aperture 74 into contact with side walls of the branch vessel 30 surrounding the ostium of the branch vessel 30 such as, for example, the carina 29. The dilation catheter 32 is then deflated and removed. Additional treatment of vessel bifurcation 26 can take place using additional stents, balloon catheters, or other structures and devices that extend, for example, into the branch vessel 30 and overlap with the expandable structure 76 surrounding the branch aperture 74.

FIGS. 15-18 illustrate another example catheter assembly 100 that 15 includes a main catheter shaft 12, a main balloon 16, and a branch balloon 18 that is positioned on and extends radially outward from the main balloon 16. The main catheter shaft 12 defines an inflation lumen 50 that is in fluid communication with the main and branch balloons 16, 18. The main balloon 16 includes distal and proximal ends 44, 46. A main guidewire lumen 48 extends through the main balloon 16. The main balloon distal end portion 44 is secured to the main guidewire lumen 48, and the proximal end portion 46 is connected to the main catheter shaft 12.

Figure 17:
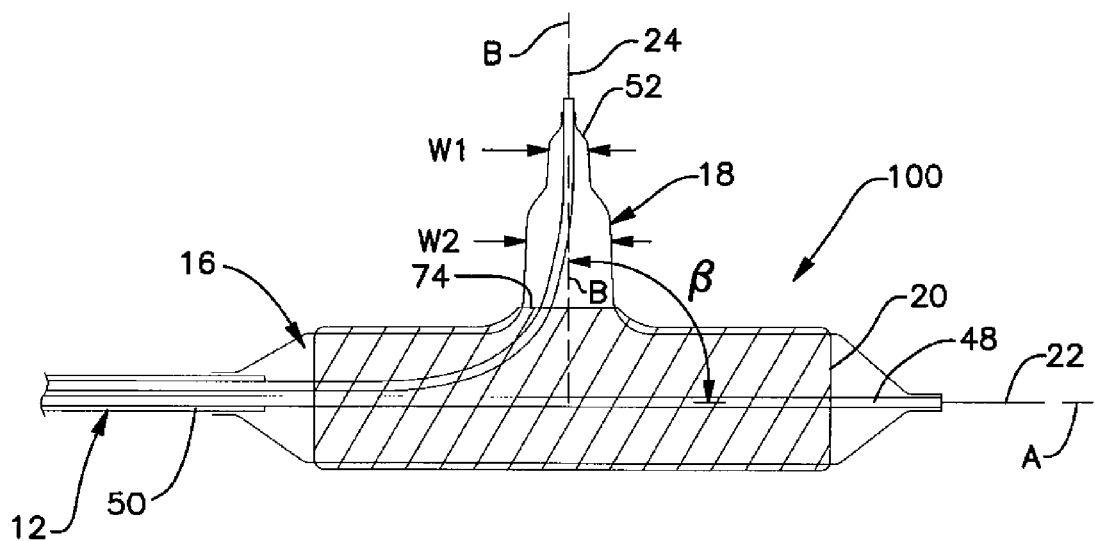
FIG. 17 is a schematic side view of the example catheter assembly shown in FIG. 15 with the main and branch balloons in an inflated state.
Figure 18:
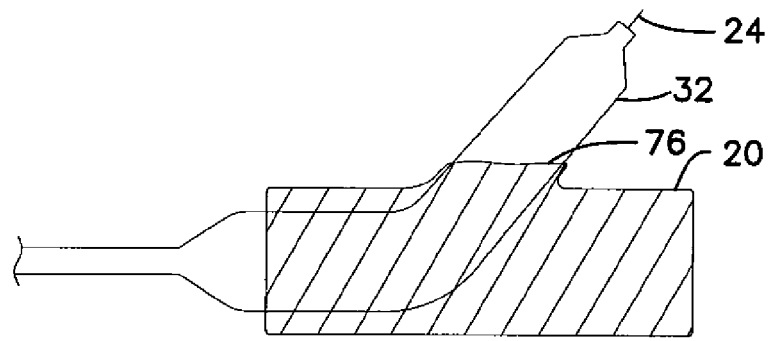
FIG. 18 is a schematic side view of the stent of the catheter assembly shown in FIG. 15 further expanded with a post delivery dilation catheter.
Figure 19:
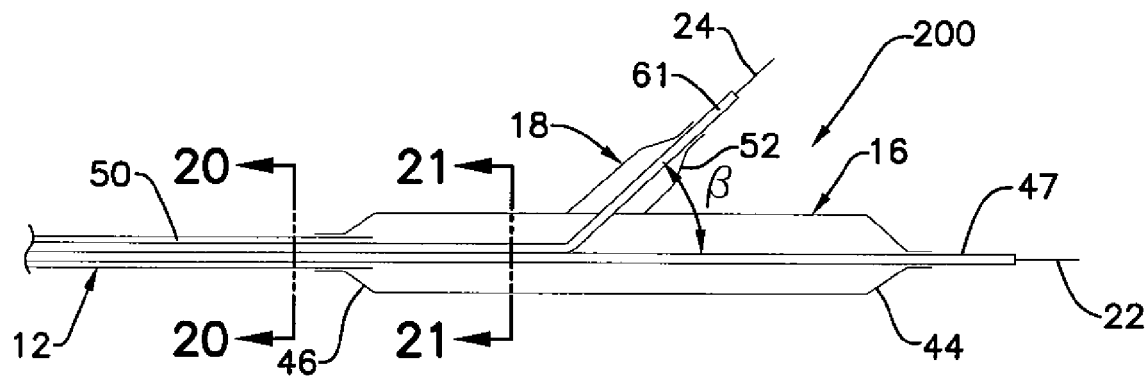
FIG. 19 is a schematic side view of another example catheter assembly in accordance with the present disclosure, wherein the main balloon and branch balloon are both in an inflated state and the branch guidewire member and main guidewire members are secured together proximal of the main balloon.
Figure 25:
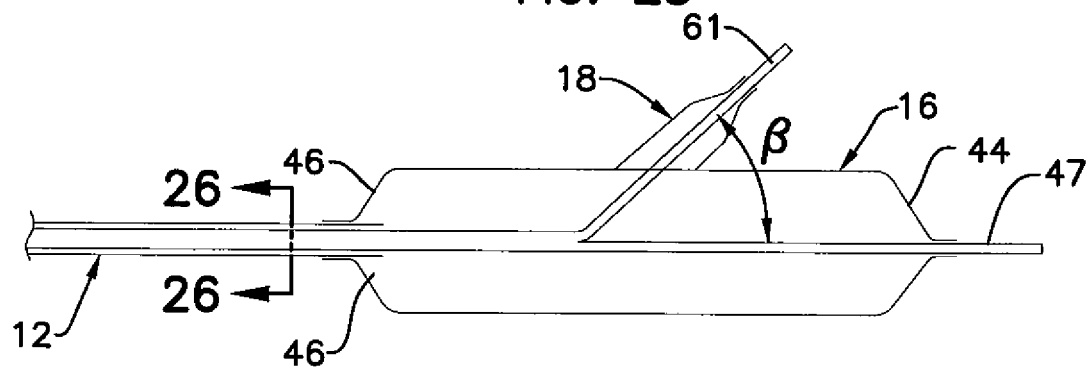
FIG. 25 is a schematic side view of another example catheter assembly in accordance with the present disclosure, wherein the main and branch guidewire lumens and the inflation lumens are defined in a single catheter member.
Figure 28:
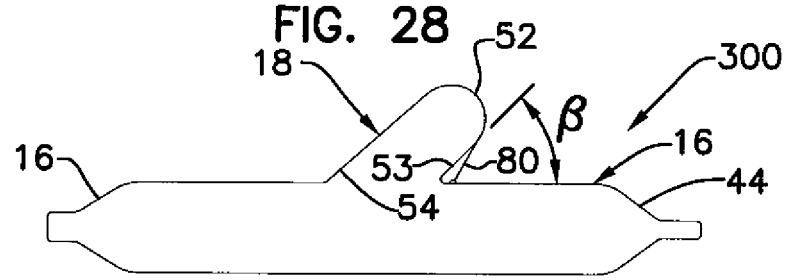
FIG. 28 is a schematic side view of another example balloon arrangement that includes a side balloon positioned on a main balloon with one side of the side balloon tethered to the main balloon.
Figure 29:
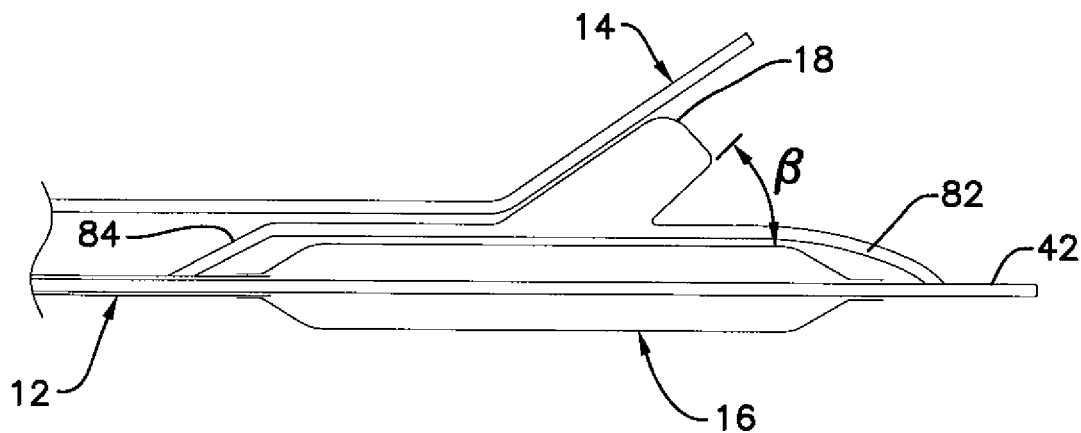
FIG. 29 is a schematic side view of another example catheter assembly in accordance with the present disclosure, wherein the side balloon is positioned on a side inflation lumen separate from the branch catheter.

The branch balloon 18 includes distal and proximal ends 52, 54, a first portion 56, and a second portion 58. The branch balloon 18 extends radially from the main balloon 16 at an angle β measured between a central longitudinal axis A of the main balloon 16 and a central longitudinal axis B of the branch balloon 18 (see FIG. 17). The angle β is typically between about 20° and about 90°. FIG. 17 illustrates an angle of about 90°. FIGS. 19, 25 and 28 illustrate an angle of about 60°. FIG. 29 illustrates an angle of about 45°. The main balloon 16 functions as the base portion 60 for the branch balloon 18 (e.g., see description above for catheter assembly 10) for holding the branch balloon 18 within the stent 20 when the main and branch balloons 16, 18 are inflated.

The first and second portions 56, 58 define first and second maximum width dimensions $W_1$, $W_2$ measured around an outer periphery at different longitudinal positions along the branch balloon 18. Typically, the width $W_1$ is less than the width $W_2$. The widths $W_1$, $W_2$ are typically less than a maximum internal width dimension $W_5$ of the branch vessel into which the balloon 18 is inserted. However, in some arrangements, one or both of the widths $W_1$, $W_2$ are at least the same size as the internal width dimension of the branch vessel into which the balloon 18 is inserted. When the width $W_1$ is smaller than the branch vessel internal width dimension, it can be easier to insert the branch balloon 18 into the branch vessel of a vessel bifurcation. The greater width $W_2$ can minimize spacing between the second portion 58 and the branch vessel into which the branch balloon 18 is inserted to improve resistance by the balloon 18 to axial and radial movement of the catheter assembly 100 relative to the vessel bifurcation.

A method of using the catheter assembly 100 to treat a vessel bifurcation (e.g., vessel bifurcation 26 having main and branch vessels 28, 30 shown in FIGS. 1-5) is now described with reference to FIGS. 15-18. The main guidewire 22 is positioned within the main vessel 28 distally beyond an ostium of the branch vessel 30. The branch guidewire 24 is positioned within the branch vessel 30 distally beyond the ostium of the branch vessel 30. A proximal end portion of the guidewire 22 is inserted into the distal end portion 44 of the main balloon 16 and a proximal end portion of the guidewire 24 is inserted into the distal end portion 52 of the branch balloon 18. The catheter assembly 100 is advanced over the guidewire 22 to a position traversing the ostium into branch vessel 30. A proximal end portion (not shown) of the main catheter shaft 12 is coupled to a manifold (not shown) that controls delivery of inflation fluid to and from the main and branch balloons 16, 18. The catheter assembly 100 is oriented radially and axially relative to the branch vessel 30 such that the branch aperture 74 and branch balloon 18 are facing the ostium of branch vessel 30. Inflation fluid is delivered to the main and branch balloons 16, 18. The branch balloon 18 is typically inflated into the inflated state shown in FIG. 16 prior to inflating of the main balloon 16 into the inflated state (see FIG. 17). The inflated branch balloon 18 extends through the branch aperture 74 into the branch vessel 28 to help axially and radially orient the stent 20 relative to the ostium of the branch vessel 24. The pressure within the main balloon 16 resulting from further delivery of inflation fluid increases sufficiently to expand the stent 20 into the expanded state shown in FIG. 17.

As discussed above, the stent 20 is typically secured to the main balloon 16 using, for example, a crimping technique. Securing the stent 20 and balloon 16 together provides a fixed axial and radial orientation of the branch balloon 18 relative to the side opening 74 in the stent 20 as the balloons 16, 18 are expanded.

After the stent 20 has been fully expanded into engagement with the main vessel 28, the main and branch balloons 16, 18 are deflated by removal of inflation fluid through the main catheter shaft 12. The deflated catheter assembly 100 is removed proximally from the stent 20. The shape of the branch balloon 18, means of attachment of the branch balloon 18 to the main balloon 16, and the angle at which the branch balloon 18 extends relative to the main balloon 16 can all contribute to improved ease in retracting the catheter assembly 100 from the stent 20.

After removal of the catheter assembly 100 from the stent 20, a dilation catheter 32 is advanced over the guidewire 24 (or a different guidewire that has been advance through the branch aperture 74 of stent 20) through an interior of the stent 20 and out of the branch aperture 74 into the branch vessel 30. The dilation catheter 32 is inflated to expand the expandable structure 76 surrounding the branch aperture 74. Preferably, the dilation catheter 32 expands the expandable structure 76 into engagement with the branch catheter 30, in particular, the carina 29 of vessel bifurcation 26 at the distal juncture between the main and branch vessels 28, 30 (see FIG. 5). The dilation catheter 32 is then deflated and removed proximally.

The vessel bifurcation 26, after post-dilation treatment by dilation catheter 32, can be further treated with other stents, inflatable balloons, or other devices and methods. For example, a separate branch stent can be inserted through the branch aperture 74 into the branch vessel 30 and expanded. Preferably, the additional branch stent overlaps with the expandable structure 76 to provide a substantially continuous structure of stent material between the stent 20 and the branch stent positioned within the branch vessel 30. Alternatively, expansion of the expandable structure 76 can be performed using the separate branch stent rather than the dilation catheter 32.

Figure 15:
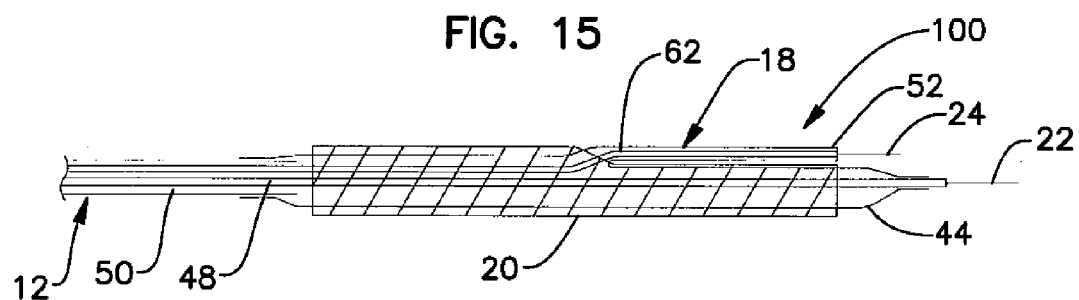
FIG. 15 is a schematic side view of another example catheter assembly in accordance with the present disclosure, wherein the main balloon and branch balloon are both in a deflated state and the branch balloon includes a branch guidewire lumen.
Figure 16:
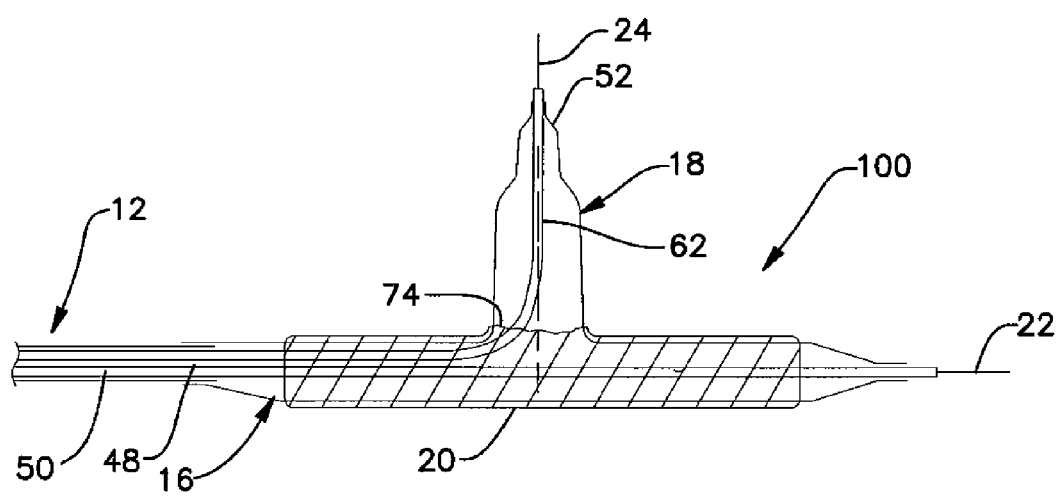
FIG. 16 is a schematic side view of the example catheter assembly shown in FIG. 15 with the branch balloon in an inflated state and the main balloon in a deflated state.

In another arrangement related to catheter assembly 100, a longitudinal position of the main guidewire 22 is fixed relative to the main balloon 16. In one example, the main guidewire lumen 48 can be eliminated completely and the distal end of the main balloon 16 is secured directly to the main guidewire 22 instead of the main guidewire lumen 48. In another example, the main guidewire lumen 48 extend to a location proximal of the distal end of the main balloon 16 (e.g., to a distal end of the main catheter shaft 12) and the distal end of the main balloon 16 is secured directly to the main guidewire 22. In a still further example, the main guidewire lumen 48 remains positioned as shown in FIGS. 15-17 and the main guidewire 22 is secured to the main guidewire lumen 48 to fix a longitudinal position of the main guidewire 22 relative to the main balloon 16.

Figure 20:
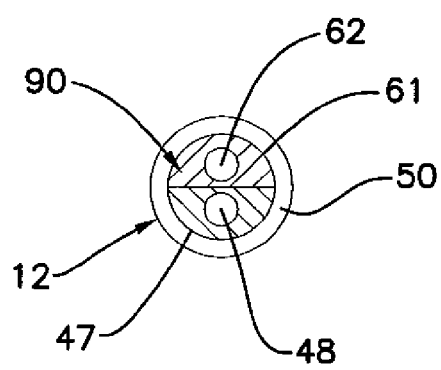
FIG. 20 is a schematic cross-sectional view of the catheter assembly shown in FIG. 19 taken along cross-sectional indicators 20-20.
Figure 21:
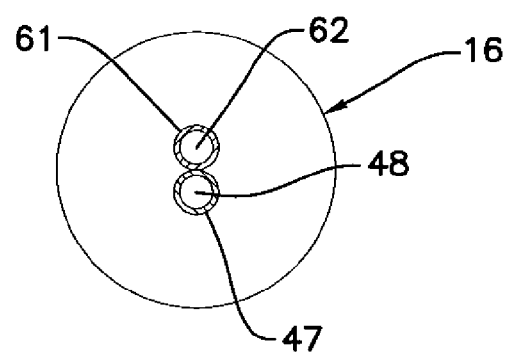
FIG. 21 is a schematic cross-sectional view of the catheter assembly shown in FIG. 19 taken along cross-sectional indicators 21-21.

Another example catheter assembly 200 is now described with reference to FIGS. 19-21. Catheter assembly 200 is similar to catheter assembly 100 in that the branch balloon 18 is positioned on the main balloon 16 and the branch guidewire lumen 62 extends through the branch balloon 18 to a distal end portion 52 of the branch balloon 18. The branch guidewire lumen 62 is sized to advance over a branch guidewire 24 when the catheter assembly 200 is used for treatment of a vessel bifurcation (e.g., see vessel bifurcation 26 in FIGS. 1-5). The main guidewire 22 is typically positioned within a main branch of the vessel bifurcation and the branch guidewire 24 is positioned within a branch vessel of the vessel bifurcation. The catheter assembly 200 in the deflated state shown (not shown) is advanced over the main and branch guidewires 22, 24 to a treatment site of the vessel bifurcation.

FIG. 19 illustrates the branch balloon 18 inflated about the branch guidewire housing 61 and extending at an angle β relative to the main balloon 16. The main balloon 16 is shown inflated about the main guidewire housing 47. As discussed above with reference to catheter assembly 100, the branch balloon 18 can inflate into the extended position shown in FIG. 20 before the main balloon 16 inflates, at the same time the main balloon 16 inflates, or after the main balloon 16 inflates.

The guidewire housings 47, 61 can be secured together along at least a portion of their length. FIG. 20 illustrates a cross-section of the catheter shaft 12 and guidewire housings 47, 61 at a location proximal of the main balloon 16. The guidewire housings 47, 61 are combined as a single guidewire shaft 90. Some configurations for the guidewire shaft 90 provide a reduced overall profile for the guidewire housings 47, 61 as compared to using two separate guidewire shafts (e.g., see the stacked guidewire housings 47, 61 in FIG. 20). The use of a single guidewire shaft 90 can also provide an overall circular cross-section for the combined guidewire housings 47, 61. The guidewire shaft 90 can be formed as, for example, an extruded member or a co-molded member. The guidewire shaft 90 can be transitioned in shape and size into to separate shafts that define the guidewire housings 47, 61 as shown in the cross-section of FIG. 21. The guidewire housings 47, 61 are preferably shaped as separate shaft members at their distal ends to provide a generally circular outer circumference surface against which the distal ends 44, 52 of the balloons 16, 18, respectively, can be secured to provide a fluid tight connection.

Figure 22:
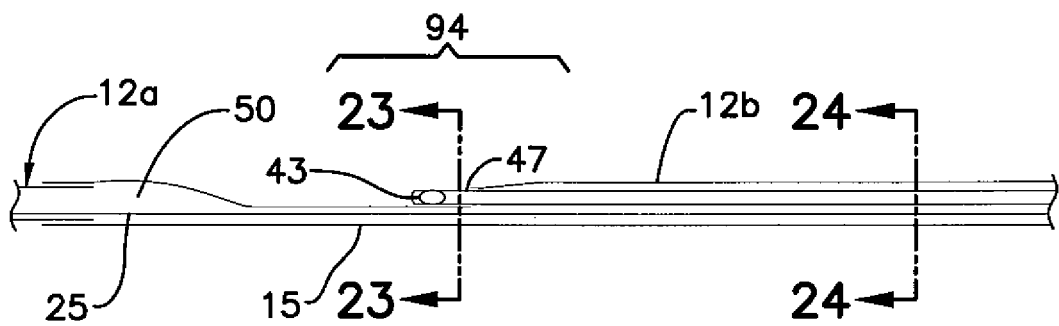
FIG. 22 is a schematic side view of a port bond arrangement for a catheter assembly.
Figure 23:
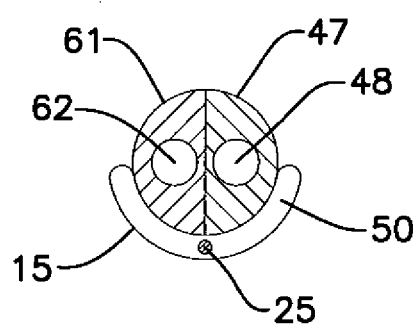
FIG. 23 is a schematic cross-sectional view of the port bond arrangement shown in FIG. 22 taken along cross-sectional indicators 23-23.
Figure 24:
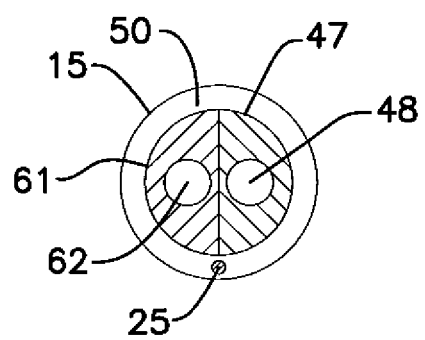
FIG. 24 is a schematic cross-sectional view of the port bond arrangement shown in FIG. 22 taken along cross-sectional indicators 24-24.

FIGS. 22-24 illustrate aspects of a port bond arrangement 92 for use in a catheter assembly such as the assembly 200 described above. The port bond arrangement provides a pair of rapid exchange (Rx) ports for the guidewires 22, 24 at a location proximal of the main balloon 16 and distal of a proximal end portion (not shown) of the catheter shaft 12. The rapid exchange ports for the guidewires 22, 24 can be positioned adjacent to each other or axially spaced apart from each other. FIG. 22 illustrates a first guidewire port 43 positioned along one side of the port bond arrangement 92 at a proximal end portion of a main guidewire housing 47. A second guidewire port (not shown) can be positioned on a side opposite the port 43 at a proximal end portion of a branch guidewire housing 61. FIG. 23 illustrates one arrangement for the main and branch guidewire housings 47, 61 combined as a single guidewire shaft 90. In other arrangements, the guidewire housings 47, 61 can be separate shaft members having a generally circular cross-section.

The port bond arrangement 90 includes first and second catheter shaft 12a, 12b. The first catheter shaft 12a can be, for example, any desired hypotube structure. The second catheter shaft 12b can be referred to a as midshaft member that spans between the first catheter shaft 12a and the main balloon 16. The second catheter shaft 12b includes a guidewire bond region 94 wherein the guidewire housings 47, 61 are exposed to provide access to the Rx ports (e.g., port 43). The second catheter shaft 12b defines an inflation lumen 50 that is in fluid communication with the balloons 16, 18 and an inflation lumen (not numbered) defined by the first catheter shaft 12a. FIG. 23 illustrates an example configuration for the inflation lumen defined by the second catheter shaft 12b at a location just distal of the guidewire port 43. FIG. 24 illustrates an example configuration for the inflation lumen 50 at a location distal of the guidewire bond region 94. Other configurations for the inflation lumen 50 and the guidewire bond region 94 are possible.

The port bond arrangement 90 can further include a core wire 25 that extends through inflation lumens defined by the first and second catheter shafts 12a, b. The core wire 25 can provide support and rigidity for the port bond arrangement 90 and the catheter assemblies 100, 200 generally. The core wire 25 can be positioned permanently using, for example, welding or adhesives, or can be a separately insertable and removable member.

Figure 26:
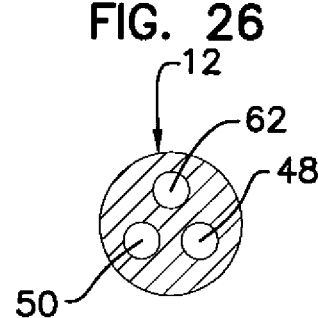
FIG. 26 is a schematic cross-sectional view of the catheter assembly shown in FIG. 25 taken along cross-sectional indicators 26-26.
Figure 27:
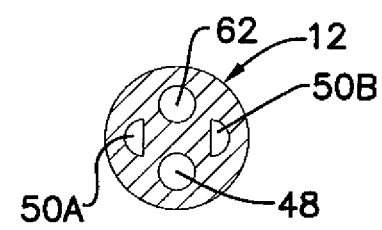
FIG. 27 is a schematic cross-sectional view of another example configuration of the catheter assembly shown in FIG. 25.

Referring now to FIGS. 25-27, an alternative catheter shaft configuration is described with reference to a combined main balloon 16 and branch balloon 18 arrangement. As shown in the cross-sectional view of FIG. 26, the catheter shaft 12 can define an inflation lumen 50, a main guidewire lumen 48, and a branch guidewire lumen 62 along at least that portion of the catheter shaft 12 that is proximal of the main balloon 16. At a location within the main balloon 16, the catheter branch 12 is divided into at least a main guidewire housing 47 that defines the main guidewire lumen 48, and a branch guidewire housing 61 that defines the branch guidewire lumen 62. The guidewire shaft 12 can include a least one inflation lumen port in fluid communication with the inflation lumen 50 and exposed within an interior of the main balloon 16 to provide inflation of the balloons 16, 18.

FIG. 27 illustrates an alternative configuration for the catheter shaft 12. The catheter shaft 12 in FIG. 27 defines main and branch guidewire housings 47, 61 and two inflation lumens 50A, 50B. Alternative numbers of lumens and arrangements of lumens in the catheter shaft 12 are possible. In one arrangement, both of the lumens 50A, 50B are in fluid communication with both the main balloon 16 and branch balloon 18. In other arrangements, one of the inflation lumens 50A, 50B is in fluid communication with only the main balloon 16 and the other of the inflation lumens 50A, 50B is in fluid communication only with the branch balloon 18. The catheter shaft 12 shown in FIGS. 25-27 can be made using, for example, extruding or molding techniques.

FIG. 28 illustrates a balloon arrangement 300 that includes a main balloon 16 and a branch balloon 18. The branch balloon 18 is positioned at a location between proximal and distal ends 44, 46 of the main balloon 16. The branch balloon 18 can be co-molded with the main balloon 16. Alternatively, the branch balloon 18 can be formed as a separate member that is mounted to the main balloon 16 in a separate assembly step. The branch balloon 18 extends in a direction generally radially away from the main balloon 16. In some cases, there may be challenges involved in providing the branch balloon 18 at an angle β that is less than 90°, particularly when using molding techniques or methods of mounting a separately formed branch balloon 18 to an exterior of the main balloon 16. One way to obtain an inflated arrangement of the branch balloon 18 at an angle β less than 90° is to first position the branch balloon 18 on the main balloon 16 so the branch balloon 18 extends at any desired angle β when inflated (e.g., 90°), and then tether one side of the branch balloon 18 to the main balloon 16 with a tether member 80. FIG. 28 illustrates the tether member 80 secured at a top end portion 52 of the branch balloon along a distal facing side 53 of the branch balloon 18. The length of the tether member 80 is less than a maximum length of the branch balloon 18 measured between the distal end 52 and a proximal end 54. The tether member 80 tends to pull the branch balloon 18 in a distal direction when the branch balloon 18 is inflated to orient the branch balloon 18 at an angle β less than 90°.

The tether member 80 can be secured to the main and branch balloons 16, 18 in a variety of ways using, for example, adhesives, laser welding, and co-molding techniques. The use of multiple tether members 80 for a single branch balloon 18 is also possible. The tether member 80 can also be secured at multiple locations along the length of the branch balloon 18, and may not in some arrangements be secured to the main balloon 16. The tether member 18 can also be used in other balloon arrangements such as the balloon arrangement described below with reference to FIG. 29, wherein the branch balloon 18 is positioned on a separate side inflation member.

FIG. 29 illustrates an alternative balloon arrangement that includes a main balloon 16 and a branch balloon 18, wherein the branch balloon 18 is positioned on a separate side inflation member 85. The side inflation member 85 includes a distal portion 82 having a proximal end thereof secured in fluid communication with the branch balloon 18 and a distal end thereof secured to the main guidewire housing 47 at a location distal of the main balloon 16. The side inflation member 85 also includes a proximal portion 84 having a distal end thereof secured in fluid communication with the branch balloon 18 and a proximal end thereof secured to the catheter shaft 12 at a location proximal of the main balloon 16. The branch balloon 18 extends at an angle β less than 90° relative to a longitudinal dimension of the main balloon 16. The angled configuration of the branch balloon 18 can be provided using, for example, the molding or tethering techniques described above with reference to the remaining Figures.

The angled arrangement of the branch balloon 18 can help maintain a branch catheter 14 in proper radial alignment with the main and branch balloon 16, 18 during inflation of the balloons 16, 18. Proper radial alignment of the branch catheter 14 sometimes includes positioning the branch catheter 14 along a proximal side surface of the branch balloon 18 during inflation of the main and branch balloon 16, 18 as shown in FIG. 29, which can help maintain proper radial and axial alignment of features of the stent (not shown) being expanded by the balloons 16, 18 relative to features of the vessel bifurcation being treated.

In the example catheter assemblies described above, the branch balloon can include a lubricious coating on an exterior surface thereof. The coating can promote insertion of the branch balloon into the branch vessel of a vessel bifurcation. The coating can also improve removal of the branch balloon from the branch vessel and the branch aperture of the stent when deflating and removing the catheter assembly from the vessel bifurcation after expansion of the stent. Some example coating for use with the branch balloon include hydrophilic polymers such as polyarylene oxides, polyvinylpyrolidones, polyvinylalcohols, hydroxyl alkyl cellulosics, algins, saccharides, caprolactones, and the like, and mixtures and combinations thereof. Hydrophilic polymers can be blended among themselves or with formulated amounts of water insoluble compounds (including some polymers) to yield coating with suitable lubricity, bonding and solubility. In some examples, portions of the devices described herein can be coated with a hydrophilic polymer or a fluoropolymer such as polytetrafluoroethylene (PTFE), better known as TEFLON®.

The branch balloons 18 described herein can be made as separate pieces that are attached to either a branch catheter shaft (catheter assembly 10) or main balloon (catheter assemblies 100, 200) in a separate step. Alternatively, the branch balloon can be formed from a branch catheter shaft or a main balloon in a molding process that results in an integral piece. In one example process, the branch balloon is molded from an extruded tube as is typical in the art. The extruded tube can be ground or otherwise reduced in thickness in advance of or after the molding step to create uniform thickness of material along the length of the branch balloon regardless of the width of the branch balloon. In one example, the thickness of the material for branch balloon is about 0.003 to about 0.01 inches when in an inflated state.

The overall structure of branch balloon 18 provides for insertion into the branch vessel 30 when being inflated and during inflation of the main balloon 16 without obstruction. Further, the branch balloon 18 has sufficient stiffness to resist bending when rotational and axial forces are applied to the inflated branch balloon 18 during inflation of the main balloon 16. The stiffness of the branch balloon 18 is dependent upon at least the following parameters: thickness of the material of the branch balloon 18, the type of attachment to the main balloon (catheter assemblies 100, 200) or to the branch catheter shaft (catheter assembly 10), the width, length, and cross-sectional shape of the branch balloon 18, and the type of material used in the branch balloon 18. The branch balloon 18 is also structured to avoid dilating the branch vessel 30. The width and compliance of the branch balloon 18 are two parameters that can influence whether the branch balloon 18 dilates the branch vessel 30. Typically, the branch balloon 18 is configured as a semi-compliant balloon.

While the example stent delivery systems 10, 100 described above illustrate a balloon expandable stent having a predetermined branch aperture, other types of stents can be used with the catheter features described above. A variety of stents can be used with the systems and methods disclosed herein. Examples of such stents can be found in, for example, in U.S. Pat. Nos. 6,210,429 and 6,325,826 to Vardi et al., and co-pending U.S. patent application Ser. No. 10/644,550, filed on Aug. 21, 2003, and titled "Stent With a Protruding Branch Portion For Bifurcated Vessels," the entire contents of which are incorporated herein by reference. In general, the aforementioned stents have a tubular shape with a continuous sidewall that extends between the proximal and distal ends. Proximal and distal stent apertures are defined at respective proximal and distal ends of the stent. A branch aperture is defined in the sidewall of the stent. The branch aperture provides access between an interior of the stent and an exterior of the stent. In some stents, the branch aperture includes expandable structure around a peripheral edge thereof that expands in a generally radial outward direction relative to a longitudinal axis of the stent. The expandable structure can be configured to extend into the branch lumen of the bifurcation upon expansion of the stent. The stent includes a plurality of strut structures that define the sidewall. The struts are expandable from a first, unexpanded state to a second, expanded state. Typically, the stent is configured to maintain the expanded state. The struts define a plurality of cell openings or cells along a length of the stent. The size and shape of the cells is typically different than the size and shape of the branch aperture. The stent is typically expanded once the stent is properly positioned in the main lumen of the bifurcation with the branch aperture aligned radially and axially with an opening into the branch lumen. The stent, including the expandable structure surrounding the branch aperture, can be expanded with a single expansion or with multiple expansions using, 10 for example, one or more inflatable balloons.

Figure 30:
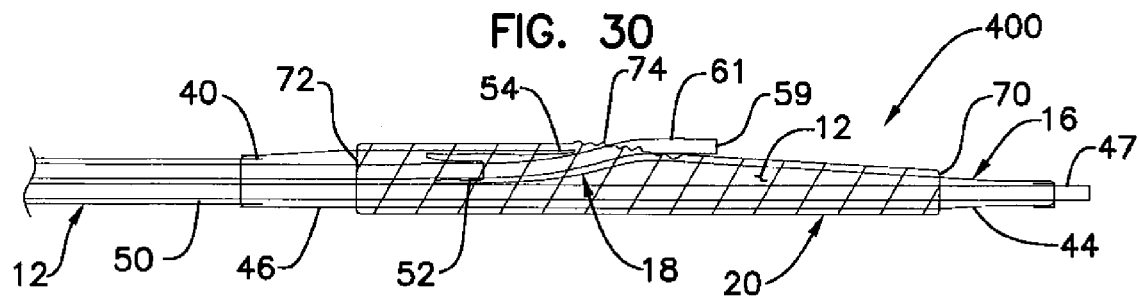
FIG. 30 is a schematic side view of another example catheter assembly in accordance with the present disclosure, wherein the branch balloon is retractable into an internal volume of the main balloon prior to inflation of the main and branch balloons.
Figure 31:
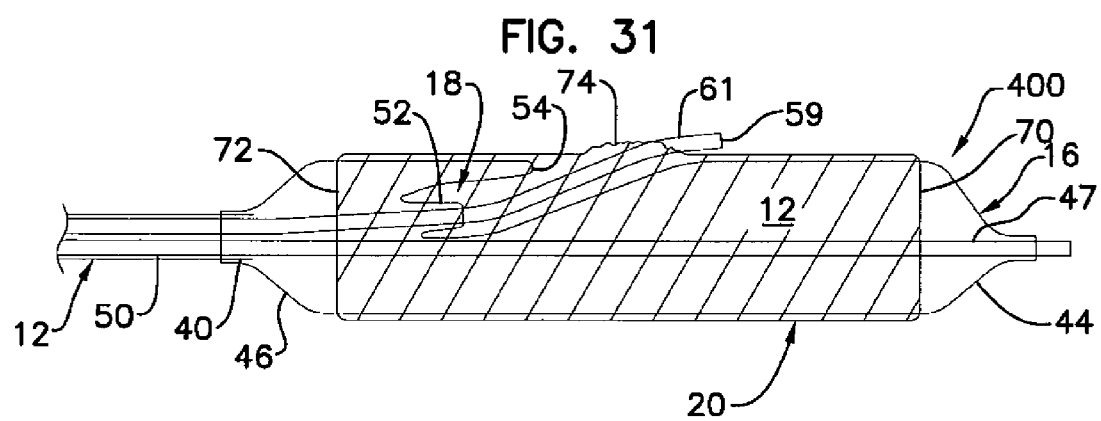
FIG. 31 is a schematic side view of the example catheter assembly of FIG. 30 with the main balloon inflated.
Figure 32:
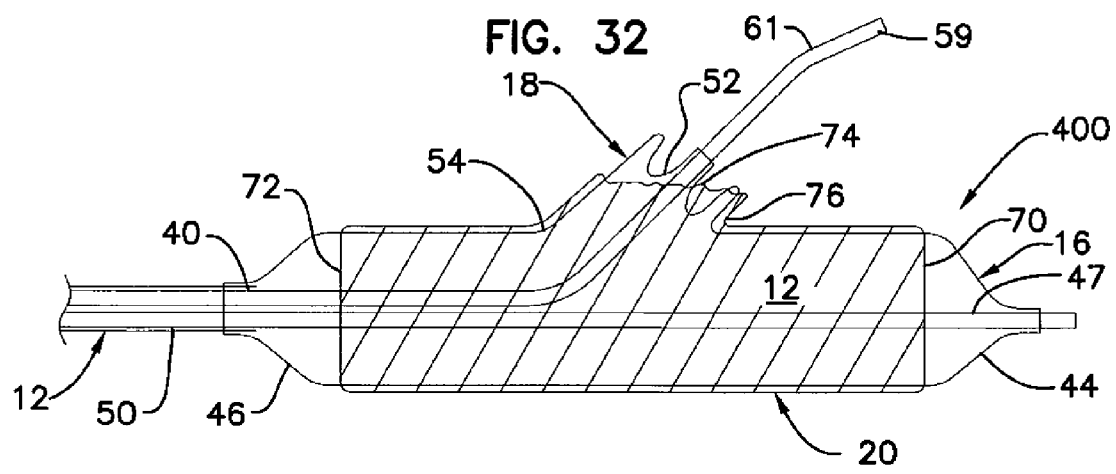
FIG. 32 is a schematic side view of the example catheter assembly of FIG. 30 with the main balloon inflated and the side balloon partially inflated.
Figure 33:
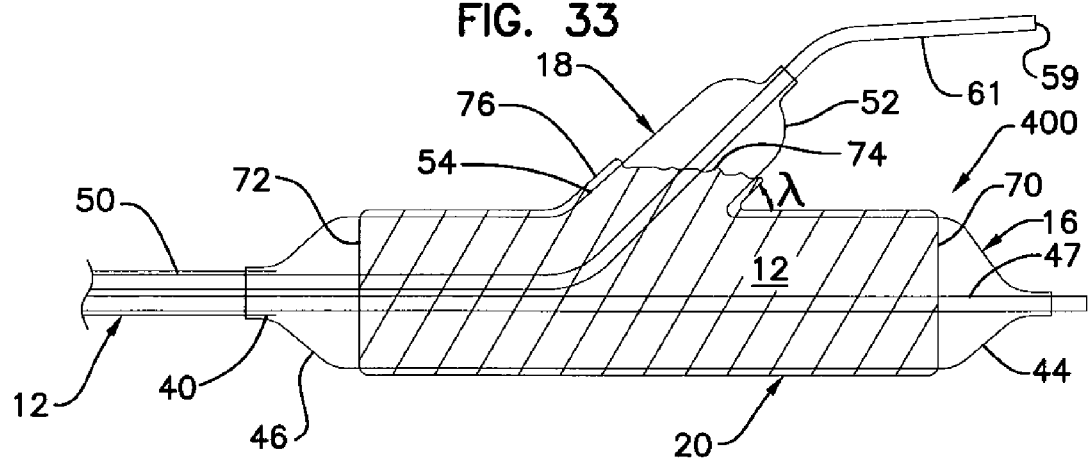
FIG. 33 is a schematic side view of the example catheter assembly of FIG. 30 with the main and side balloons inflated.
Figure 34:
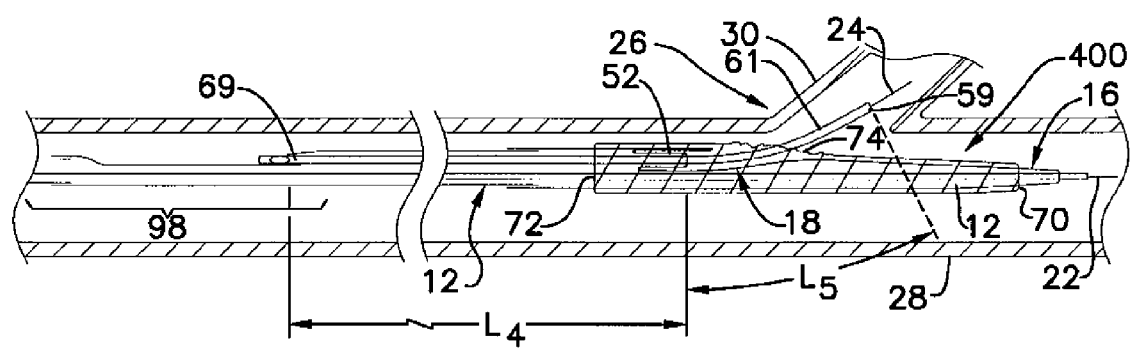
FIG. 34 is a schematic side view of the example catheter assembly of FIG. 30 positioned to treat a vessel bifurcation.

FIGS. 30-34 illustrate another example catheter assembly 400 that includes a main catheter shaft 12, a main balloon 16, a branch balloon 18, and a stent 20. The catheter assembly 400 can be used with a main guidewire 22 and a branch guidewire 24 that help position the catheter assembly 400 relative to features of a vessel bifurcation during use. The branch balloon 18 is retractable into an internal volume of the main balloon 16 as shown in FIGS. 30, 31, and 34. Delivering inflation fluid to the main balloon 12 inflates the main balloon to expand the stent 20. Further delivery of inflation to the main balloon 12 causes the branch balloon 18 to inflate and protrude out of the main balloon 12, through the stent 20, and radially outward into an extended position relative to the main balloon 12. The branch balloon 18 can be configured to retract back into the main balloon 12 when deflated. Further details concerning the operation and features of the catheter assembly 400 are provided in the following description.

The main catheter shaft 12 includes a distal end 40. The main balloon 16 is positioned extending from the distal end 40 of the main catheter shaft 12. The main balloon 16 includes distal and proximal ends 44, 46, and a main guidewire housing 47 that extends continuously from at least the distal end 40 of the main catheter shaft 12 to the distal end 44 of the main balloon 16. Typically, a proximal end 46 of the main balloon 16 is mounted to the main catheter shaft 12 while the distal end 44 of the main balloon 16 is mounted to the main guidewire housing 47.

The branch balloon 18 includes distal and proximal ends 52, 54, a branch 5 guidewire housing 61 having a distal end 59 and a proximal end 69 (see FIG. 34). The branch balloon 18 can be formed integral with the main balloon 16 using, for example, a vacuum molding process. In other examples, the branch balloon 18 can be separately formed and later secured to the main balloon 16 in a separate step using, for example, heat welding or laser welding of the proximal end 54 of the branch balloon 18 to the main balloon 16 at a location positioned between the distal and proximal ends 44, 46 of the main balloon 16. The distal end 52 of the branch balloon 18 is typically secured to the branch guidewire housing 61.

In one example arrangement, the proximal end 69 of the guidewire housing 61 exits the main catheter shaft 12 at a rapid exchange port area 98. The rapid exchange port area 98 is typically positioned at a distance $L_4$ from the distal end 52 of the branch balloon 18 as shown in FIG. 34. The location of the rapid exchange port area 98 can also be determined relative to the distal end 59 of the branch guidewire housing 61, which is a distance $L_4$ plus a distance $L_5$ as shown in FIG. 34, wherein the distance $L_5$ is the distance measured from the distal end 52 of the branch balloon 18 to the distal end 59 of the branch guidewire housing 61. A distance $L_4$ is typically in the range of about 50 to about 300 millimeters, and more preferably in the range of about 50 to about 200 millimeters. The distance $L_5$ is typically in the range of about 10 to about 100 mm, and more preferably about 10 to about 20 mm.

In other arrangements, a separate rapid exchange port area can be provided for the main guidewire housing 47 at a distal end thereof. In one example, the rapid exchange port area for the main guidewire housing 47 is positioned within the same rapid exchange port area as the branch guidewire housing 61.

The stent 20 includes distal and proximal ends 70, 72, a side opening 74, and an expandable portion 76 that defines the side opening 74. The expandable portion 76 is configured to expand radially outward into, for example, a branch vessel at a vessel bifurcation (see FIG. 30). The stent 20 is positioned on the main balloon 16 with the side opening 74 aligned with the location on the main branch 16 where the branch balloon 18 extends radially outward as shown in FIGS. 32 and 33.

The catheter assembly 400 can be used to treat a vessel bifurcation 26 that includes a main vessel 28 and a branch vessel 30 extending from the main vessel 28 as shown in FIG. 34. Typically, when treating a vessel bifurcation 26, the catheter assembly 400 is arranged with the main balloon 16 and stent 20 positioned within the main vessel 28 and the side opening 74 of the stent 20 arranged facing an opening into the branch vessel 30. Later inflation of the main and branch balloons 16, 18 result in the expandable portion 76 of the stent 20 extending into the branch vessel 30 while the body of the stent 20 remains in the main vessel 28.

Providing a catheter assembly wherein the branch balloon is retractable into the main balloon, otherwise described as an invaginated branch balloon, makes it possible to maintain the branch balloon entirely within the stent prior to inflation of the main and branch balloons. Using a retractable branch balloon in combination with a branch guidewire housing that extends through the side opening in the stent and into a branch vessel can provide improved axial and radial alignment of the stent side opening relative to the branch vessel prior to and during inflation of the main and branch balloons, while also providing a path along which the branch balloon can travel as the branch balloon extends from within the main balloon when uninflated (see FIGS. 30 and 31) to a radially outward extending position when fully inflated (see FIG. 33). As the branch balloon is inflated and begins to move from within the main balloon through the side opening 74 of the stent 20, the expandable portion 76 (also referred to as "petals") are also moved in a radially outward direction.

In other arrangements when at least a portion of the side balloon extends through the side opening 74 prior to inflation of the side balloon (e.g., see catheter assembly 100 shown in FIGS. 15-17) inflation of the side balloon might result, in some instances, in bending or otherwise moving portions of the expandable portion 76 of the stent 20 in a radial inward direction or in a primarily longitudinal direction. Particularly, that portion of the expandable portion 76 oriented on a distal side of the side opening 74 can be more susceptible to deformation and/or movement in some direction other than a radial outward direction and into the branch vessel.

A common orientation of the branch vessel 30 relative to the main vessel 28 is extending at an acute angle such as shown in FIG. 34. Therefore, positioning a branch balloon 18 on the main balloon 16 so that the branch balloon 18 extends at an acute angle relative to the main balloon 16 when fully inflated can help better align and engage both the branch balloon 18 and the expandable portion 76 of the stent 20 with the branch vessel 30. The angle λ (see FIG. 33) at which the branch balloon 18 extends relative to the main balloon 16 can be in the range of, for example, 0° to about 90°, and more preferably about 30° to about 60°. Orienting the branch vessel 18 at an obtuse angle relative to the main balloon 16 rather than a right angle or acute angle is less common, but is a possible arrangement within the scope of the present disclosure.

Typically, the proximal end 69 of the branch guidewire housing 61 maintains a fixed axial position relative to the main catheter shaft 12 (e.g., at the rapid exchange port area 96 shown in FIG. 34). Since the distal end 54 of the branch balloon 18 is secured to the branch guidewire housing 60, the branch guidewire housing distal end 59 should be advanced distally into the branch vessel 30 as the branch balloon 18 inflates and moves from a position internal the main balloon 16 to a position extending radially outward from the main balloon 16. In order for the branch guidewire housing 61 to axially move in a distal direction, there must either be an additional amount of slack or extra length of branch guidewire housing 61 available between the distal end 52 of the branch balloon 18 and the proximal end 69 of the branch guidewire lumen 61, or the branch guidewire lumen 61 preferably include properties that permit elongation of the branch guidewire housing 61. In one example, the branch guidewire housing 61 comprises a material with a percentage elongation capability of about 1% to about 5%, and preferably about 2% to about 3%. Thus, for a branch guidewire housing 61 having a length $L_4$ of about 200 mm, about 5 to about 10 mm of elongation is possible. This amount of elongation should be sufficient for permitting the branch balloon 18 to extend from a position within the main balloon 16 (see FIG. 30) to a position extending radially outward from the main balloon 16 (see FIG. 33) when fully inflated.

Providing a branch guidewire housing 61 with elongation properties can provide elastic characteristics that can assist in withdrawing the branch balloon 18 back into the stent 20 during deflation of the main and branch balloon 16, 18. Typically, elongation of the branch guidewire housing 61 is elastic in nature such that any percentage elongation results in recoil back to the original length. An axial force is applied to the branch guidewire housing 61 as the branch balloon 18 inflates, thereby elongating the branch guidewire housing 61. Once the branch guidewire 18 begins to deflate, the applied axial force begins to release and the elastic forces of the branch guidewire housing 61 react in an axially proximal direction thereby drawing the branch balloon 18 back through the side opening 74 of the stent 20, and sometimes back into the interior of the main balloon 16. This ability to retract the branch balloon 18 automatically can provide less chances of, for example, the branch balloon 18 catching on or deforming the stent 20 when retracting the main and branch balloons 16, 18 from the stent 20.

A method of treating a vessel bifurcation is now described with reference to FIGS. 30-34 and catheter 400. A main guidewire 22 is advanced into the main vessel 28 to a position distally beyond an opening into the branch vessel 30. A branch guidewire 24 is also advanced through the main vessel 28 and into the branch vessel 30. The catheter assembly 400 is advanced over the main and branch guidewires 22, 24 into position adjacent to the vessel bifurcation 26. The distal end 59 of the branch guidewire housing 61 extends through the side opening 74 to a position outside of the stent 20 while the stent 20 is crimped around deflated main and branch balloons 16, 18. Further distal advancement of the catheter assembly 400 advances the distal end 59 of the branch guidewire housing 61 into the branch vessel 30 and helps orient the side opening 74 of the stent in axial and radial orientation with an opening into the branch vessel 30.

With the side opening 74 oriented facing the opening into the branch vessel 30, the main balloon 16 is inflated to expand the main body of the stent into engagement with the main vessel 28 (see FIG. 31). Delivery of still further inflation fluid begins to inflate the branch balloon 18 thereby moving the branch balloon 18 from a position within the main balloon 16 radially outward through the side opening 74 (see FIG. 32) until the branch balloon 18 is fully inflated (see FIG. 33). Movement of the branch balloon 18 from the position shown in FIG. 31 to the position shown in FIG. 33 moves the expandable portion 76 of the stent 20 into a radially outward orientation and into the branch vessel 30. Such movement of the branch balloon 18 also elongates the branch guidewire housing 61 some percent elongation. With the stent expandable portion 76 extending at least partially into the branch vessel 30, the main and branch balloons 16, 18 can be deflated and withdrawn from the stent 20.

After removal of the catheter assembly 400 from the stent 20, a dilation catheter 32 can be advanced over the guidewire 22 (or a different guidewire that has been advanced through the branch aperture 74 of stent 20) through an interior of the stent 20 and out of the branch aperture 74 into the branch vessel 30. The dilation catheter 32 is inflated to expand the expandable structure 76 surrounding the branch aperture 74. Preferably, the dilation catheter 32 expands the expandable structure 76 into engagement with the branch catheter 30, in particular, the carina 29 of vessel bifurcation 26 at the distal juncture between the main and branch vessels 28, 30 (see FIG. 5). The dilation catheter 32 is then deflated and removed proximally. The vessel bifurcation 26, after post-dilation treatment by dilation catheter 32, can be further treated with other stents, inflatable balloons, or other devices and methods. For example, a separate branch stent can be inserted through the branch aperture 74 into the branch vessel 30 and expanded. Preferably, the additional branch stent overlaps with the expandable structure 76 to provide a substantially continuous structure of stent material between the stent 20 and the branch stent positioned within the branch vessel 30. Alternatively, expansion of the expandable structure 76 can be performed using the separate branch stent rather than the dilation catheter 32.

One aspect of the present disclosure relates to a catheter assembly for treatment of a vessel bifurcation. The catheter assembly includes a main catheter shaft, a stent having a branch aperture defined in a sidewall of the stent between proximal and distal ends of the stent, a main balloon, and a branch balloon. The main balloon is positioned at a distal end portion of the main catheter shaft and extends through the stent between proximal and distal ends of the stent. The branch balloon extends from within the stent adjacent the main balloon, through the branch aperture of the stent, and into a branch vessel of the vessel bifurcation when inflated. The branch balloon when inflated has a length dimension along a longitudinal direction of extension of the branch balloon that is at least as great as a maximum width dimension of the branch balloon measured perpendicular to the length dimension.

Another aspect of the present disclosure relates to a catheter assembly adapted for treatment of a vessel bifurcation. The catheter assembly includes a main catheter shaft, a main balloon, and a branch balloon. The main balloon extends from a distal end portion of the main catheter shaft within a main vessel of the vessel bifurcation. The branch balloon extends radially outward relative to the main balloon when inflated. The branch balloon has a length sufficient to extend into a branch vessel of the vessel bifurcation when the main balloon is in a deflated state and the branch balloon is in an inflated state.

A further aspect of the present disclosure relates to a method of treating a vessel bifurcation with a catheter assembly. The vessel bifurcation includes a main vessel, a branch vessel extending from the main vessel, a stent having a branch aperture between proximal and distal ends of the stent, a main catheter shaft, a main balloon at a distal end portion of the main catheter shaft, and a branch balloon. The main balloon extends between proximal and distal ends of the stent. The branch balloon extends through the branch aperture of the stent. Some of the steps of the method include positioning the catheter assembly within the main vessel with the branch aperture facing an ostium of the branch vessel, and inflating the branch balloon to extend the branch balloon from within the main vessel into the branch vessel. A further step of the method includes expanding the stent with the main balloon after inflating the branch balloon. The branch balloon maintains contact with an interior of the branch vessel to resist axial and rotational movement of the catheter assembly while the main balloon is inflated.

Another aspect of the present disclosure relates to a catheter assembly for treatment of a vessel bifurcation. The catheter assembly includes a main catheter shaft, a main balloon, a branch balloon, and first and second guidewire housings. The main catheter shaft has a proximal end portion and a distal end portion. The main balloon extends from the distal end portion of the main catheter shaft and includes a proximal end portion and a distal end portion. The branch balloon has a proximal end portion and a distal end portion, and extends in a direction radially outward relative to the main balloon. The first guidewire housing defines a first guidewire lumen and extends through a portion of the main catheter shaft and through the main balloon between the proximal and distal end portion of the main balloon. The second guidewire housing defines a second guidewire lumen and extends through a portion of the main catheter shaft, into the main balloon through the proximal end portion of the main balloon, and through the branch balloon between the proximal and distal ends of the side balloon.

A further aspect of the present disclosure relates to a catheter assembly adapted for treatment of a vessel bifurcation.

The catheter assembly includes a main catheter shaft, a main balloon, a branch balloon, and a stent. The main catheter shaft has a proximal end portion and a distal end portion. The main balloon extends from the distal end portion of the main catheter shaft and includes a proximal end portion, a distal end portion, and a main balloon interior. The branch balloon includes a proximal end portion and a distal end portion, and extends in a direction radially outward relative to the main balloon when in an inflated state. The stent includes a branch aperture positioned at a location between proximal and distal open ends of the stent. The main balloon extends within the stent from the proximal open end to the distal open end of the stent. The branch balloon extends through the branch aperture of the stent when inflated and is positioned within the stent prior to inflation. In some arrangements, the branch balloon is positioned within the main balloon interior prior to inflation. The above specification, examples and data provide a complete description of the manufacture and use of the composition of the invention. Since many embodiments of the invention can be made without departing from the spirit and scope of the invention, the invention resides in the claims hereinafter appended.

The invention claimed is:

1. A catheter assembly adapted for treatment of a vessel bifurcation, comprising:
    a main catheter shaft having a proximal end portion and a distal end portion;
    a main balloon positioned at the distal end portion of the main catheter shaft, the main balloon extending within a main vessel of the vessel bifurcation;
    a branch balloon when inflated extending radially outward at a branch angle relative to the main balloon, the branch balloon having a length sufficient to extend into a branch vessel of the vessel bifurcation when the main balloon is in a deflated state and the branch balloon is in an inflated state, wherein the branch balloon has at least three distinct sections along a length of the branch balloon, including a base section adjacent the main balloon, and first and second sections extending away from the main balloon, the base, first, and second sections each having a length, wherein the combined lengths of the base, first, and second sections is equal to a length of the branch balloon, the base, first, and second sections having different maximum width dimensions, wherein the maximum width dimension of the base section is greater than the maximum width dimension of the first and second sections;
    a main guidewire housing defining a main guidewire lumen that extends through the main balloon; and
    a branch guidewire housing that defines a branch guidewire lumen, wherein the branch guidewire housing extends through branch balloon.

2. The catheter assembly of claim 1, wherein the branch balloon is molded integral with the main balloon.

3. The catheter assembly of claim 1, further comprising a stent, the stent having a proximal open end, a distal open end, and a branch aperture, the branch aperture defined in a sidewall of the stent at a location between the proximal and distal open ends of the stent, wherein the branch balloon extends through the branch aperture when inflated.

4. The catheter assembly of claim 3, wherein the maximum width dimension of the first and second sections of the branch balloon extending outside of the stent is less than the maximum width dimension of the base section of the branch vessel, wherein the maximum width dimension of the base section is greater than a maximum width dimension of the branch aperture of the stent such that the base section is retained within the stent when the branch balloon is inflated.

5. The catheter assembly of claim 1, wherein the branch angle is within the range of 25° to 90° inclusive relative to a longitudinal axis of the main balloon.

6. The catheter assembly of claim 1, further comprising a branch catheter defining a branch guidewire lumen and having a distal end portion, wherein the branch balloon is positioned at the distal end portion of the branch catheter.

7. The catheter assembly of claim 1, further comprising a tether member, the tether member having a distal end mounted to the branch balloon and a proximal end mounted to the main balloon, wherein the tether defines in part the branch angle when the branch balloon is inflated.

8. The catheter assembly of claim 1, wherein the first and second sections each have a substantially constant circumference along a majority of their length.

9. A catheter assembly for treatment of a vessel bifurcation, the catheter assembly comprising:
    a main catheter shaft having a proximal end portion and a distal end portion;
    a main balloon extending from the distal end portion of the main catheter shaft, the main balloon having a proximal end portion and a distal end portion;
    a branch balloon, the branch balloon having a proximal end portion and a distal end portion, the branch balloon extending in a direction radially outward relative to the main balloon;
    a first guidewire housing, the first guidewire housing defining a first guidewire lumen and extending through a portion of the main catheter shaft and through the main balloon between the proximal and distal end portions of the main balloon; and
    a second guidewire housing, the second guidewire housing defining a second guidewire lumen and extending through a portion of the main catheter shaft, into the main balloon through the proximal end portion of the main balloon, and through the branch balloon between the proximal and distal ends of the branch balloon.

10. The catheter assembly of claim 9, wherein the first and second guidewire housings are formed as a single shaft that defines the first and second guidewire lumens.

11. The catheter assembly of claim 9, wherein at least a portion of the main catheter shaft and at least a portion of the first and second guidewire housings are formed as a single shaft that defines the first and second guidewire lumens.

12. The catheter assembly of claim 11, wherein the single shaft further defines an inflation lumen, the inflation lumen in fluid communication with at least the main balloon.

13. The catheter assembly of claim 9, wherein the branch balloon is integral with the main balloon.

14. The catheter assembly of claim 9, wherein the branch balloon is positioned within an interior portion of the main balloon when the branch balloon is in a deflated state, and the branch balloon is positioned exterior of the main balloon when in an inflated state.

* * * * *